(12) United States Patent
Boone et al.

(10) Patent No.: US 11,744,637 B2
(45) Date of Patent: ***Sep. 5, 2023

(54) CLOSURE ASSEMBLY THAT IS LATERALLY MOVABLE FOR SELECTIVE LOCKING

(71) Applicant: GYRUS ACMI, INC., Southborough, MA (US)

(72) Inventors: Eric J. Boone, Saint Michael, MN (US); Christian J. Fiksen, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 511 days.

This patent is subject to a terminal disclaimer.

(21) Appl. No.: 17/000,958

(22) Filed: Aug. 24, 2020

(65) Prior Publication Data

US 2021/0000535 A1 Jan. 7, 2021

Related U.S. Application Data

(63) Continuation of application No. 15/941,128, filed on Mar. 30, 2018, now Pat. No. 10,786,299.

(51) Int. Cl.
*A61B 18/14* (2006.01)
*A61B 17/29* (2006.01)
*A61B 18/00* (2006.01)

(52) U.S. Cl.
CPC ...... *A61B 18/1445* (2013.01); *A61B 17/2909* (2013.01); *A61B 2017/2946* (2013.01);
(Continued)

(58) Field of Classification Search
CPC ..... A61B 17/29; A61B 18/14; A61B 17/2909; A61B 18/1445; A61B 2017/2946;
(Continued)

(56) References Cited

U.S. PATENT DOCUMENTS

| 1,198,958 A | 9/1916 | Risley |
| 2,042,985 A | 6/1936 | Gardella |

(Continued)

FOREIGN PATENT DOCUMENTS

| EP | 0392548 A1 | 10/1990 |
| EP | 0908152 A1 | 4/1999 |

(Continued)

OTHER PUBLICATIONS

U.S. Appl. No. 15/941,128 U.S. Pat. No. 10,786,299, filed Mar. 30, 2018, Closure Assembly That is Laterally Movable for Selective Locking.

(Continued)

*Primary Examiner* — George J Ulsh
(74) *Attorney, Agent, or Firm* — Schwegman Lundberg & Woessner, P.A.

(57) ABSTRACT

A surgical device comprising: a closure assembly including: (a) a movement unit including: a bar that moves in a direction of a prescribed motion; (b) a latch unit including: (i) a latch plate including a hook latch that selectively receives the bar, the latch plate being movable in the direction of the prescribed motion between (A) a lockable state where the hook latch is engageable by the bar of the movement unit, and (B) an unlockable state where the bar does not reach the hook latch or the hook latch is moved out of alignment with the prescribed motion so that the hook latch is not engaged by the bar; and (ii) a stop that restricts movement of the movement unit relative to the hook latch.

20 Claims, 7 Drawing Sheets

(52) U.S. Cl.
CPC .............. *A61B 2018/0091* (2013.01); *A61B 2018/1455* (2013.01); *A61B 2018/1462* (2013.01); *Y10T 292/096* (2015.04); *Y10T 292/702* (2015.04)

(58) Field of Classification Search
CPC .... A61B 2018/0091; A61B 2018/1455; A61B 2018/1462; Y10T 292/096; Y10T 292/702
See application file for complete search history.

(56) References Cited

U.S. PATENT DOCUMENTS

| | | |
|---|---|---|
| 2,214,984 A | 9/1940 | Bachmann |
| 2,381,084 A | 8/1945 | Slad |
| 2,894,424 A | 7/1959 | Vaughan, Jr. |
| 3,189,374 A | 6/1965 | Mertes |
| 3,399,583 A | 9/1968 | Lance |
| 3,465,621 A | 9/1969 | Ladd |
| 3,643,663 A | 2/1972 | Sutter |
| 3,694,015 A | 9/1972 | Gley |
| 3,699,632 A | 10/1972 | Anhalt |
| 3,819,282 A | 6/1974 | Schultz |
| 3,913,586 A | 10/1975 | Baumgarten |
| 4,215,884 A | 8/1980 | Little |
| 4,318,313 A | 3/1982 | Tartaglia |
| 4,449,022 A | 5/1984 | Uno et al. |
| 4,494,543 A | 1/1985 | Hart |
| 4,792,165 A | 12/1988 | Nishimura |
| 5,104,397 A | 4/1992 | Vasconcelos et al. |
| 5,176,702 A | 1/1993 | Bales et al. |
| 5,211,655 A | 5/1993 | Hasson |
| 5,358,292 A | 10/1994 | Van Wiebe et al. |
| 5,425,743 A | 6/1995 | Nicholas |
| 5,498,039 A | 3/1996 | Bivens |
| 5,499,998 A | 3/1996 | Meade |
| 5,735,849 A | 4/1998 | Baden et al. |
| 5,884,954 A | 3/1999 | Trozera |
| 6,050,996 A | 4/2000 | Schmaltz et al. |
| 6,056,333 A | 5/2000 | Wach |
| 6,247,733 B1 | 6/2001 | Weiland |
| 6,585,735 B1 | 7/2003 | Frazier et al. |
| 6,669,250 B1 | 12/2003 | St. Louis |
| 6,799,705 B1 | 10/2004 | Lutoslawski |
| 7,115,139 B2 | 10/2006 | Mcclurken et al. |
| 7,118,587 B2 | 10/2006 | Dycus et al. |
| 7,150,749 B2 | 12/2006 | Dycus et al. |
| 7,201,411 B2 | 4/2007 | Bella et al. |
| 7,232,440 B2 | 6/2007 | Dumbauld et al. |
| 7,766,910 B2 | 8/2010 | Hixson et al. |
| 7,793,995 B2 | 9/2010 | King et al. |
| 7,802,856 B2 | 9/2010 | Hashemi et al. |
| 8,109,582 B2 | 2/2012 | Dubach |
| 8,246,094 B2 | 8/2012 | Long et al. |
| 8,328,170 B2 | 12/2012 | Wasinger |
| 8,398,620 B2 | 3/2013 | Bacher et al. |
| 8,945,175 B2 | 2/2015 | Twomey |
| 9,452,011 B2 | 9/2016 | Batchelor et al. |
| 9,851,741 B2 | 12/2017 | Lamser et al. |
| 10,786,299 B2 | 9/2020 | Boone et al. |
| 2002/0016609 A1 | 2/2002 | Wensel et al. |
| 2006/0190035 A1 | 8/2006 | Hushka et al. |
| 2006/0208506 A1 | 9/2006 | Kern et al. |
| 2008/0154300 A1 | 6/2008 | Jabbour |
| 2011/0301637 A1 | 12/2011 | Kerr et al. |
| 2012/0109187 A1 | 5/2012 | Gerhardt, Jr. et al. |
| 2012/0184989 A1 | 7/2012 | Twomey |
| 2012/0184990 A1 | 7/2012 | Twomey |
| 2012/0191091 A1 | 7/2012 | Allen |
| 2013/0066317 A1 | 3/2013 | Evans et al. |
| 2013/0178852 A1 | 7/2013 | Allen, IV et al. |
| 2013/0325057 A1 | 12/2013 | Larson et al. |
| 2014/0135805 A1 | 5/2014 | Windgassen et al. |
| 2014/0236156 A1 | 8/2014 | Arlettaz et al. |
| 2014/0276795 A1 | 9/2014 | Batchelor et al. |
| 2015/0331443 A1 | 11/2015 | Lamser et al. |
| 2016/0051275 A1 | 2/2016 | Batchelor et al. |
| 2016/0338763 A1 | 11/2016 | Allen, IV et al. |
| 2017/0196624 A1 | 7/2017 | Nagtegaal et al. |
| 2017/0367752 A1 | 12/2017 | Boudreaux et al. |
| 2019/0298437 A1 | 10/2019 | Boone et al. |

FOREIGN PATENT DOCUMENTS

| | | |
|---|---|---|
| EP | 2263586 A2 | 12/2010 |
| EP | 3545879 A1 | 10/2019 |
| EP | 3545879 B1 | 2/2021 |

OTHER PUBLICATIONS

"European Application Serial No. 21156438.0, Extended European Search Report dated May 31, 2021", 9 pgs.

"U.S. Appl. No. 15/941,128, Non Final Office Action dated Jan. 30, 2020", 10 pgs.

"U.S. Appl. No. 15/941,128, Notice of Allowance dated May 18, 2020", 7 pgs.

"U.S. Appl. No. 15/941,128, Response filed Apr. 23, 2020 to Non Final Office Action dated Jan. 30, 2020", 12 pgs.

"Endoscopic Cutting Forceps With Jaw Clamp Lever Latching Mechanism", Potentially related U.S. Appl. No. 14/706,146, filed May 7, 2015, 40 pgs.

"European Application Serial No. 19163995.4, Extended European Search Report dated Aug. 29, 2019", 7 pgs.

"European Application Serial No. 19163995.4, Response filed Mar. 24, 2020 to Extended European Search Report dated Aug. 29, 2019", 9 pgs.

"Forceps Including a Double Biased Handle Latch", Potentially related U.S. Appl. No. 15/941,590, filed Mar. 30, 2018, 48 pgs.

"Forceps Including a Pre-Loaded Handle Latch", Potentially related U.S. Appl. No. 15/941,205, filed Mar. 30, 2018, 42 pgs.

"Forceps Including a Pre-Loaded Handle Latch", Potentially related U.S. Appl. No. 15/967,491, filed Apr. 30, 2018, 40 pgs.

"HALO Cutting Forceps", Olympus, [Online] Retrieved from the internet: <http://www.olympusamerica.com/msg_section/envision/oneoffpages/files/Halo_PKS_Brochure.pdf> (Last Accessed May 14, 2018), (Apr. 3, 2014), 2 pgs.

"European Application Serial No. 21156438.0, Response filed Jan. 28, 2022 to Extended European Search Report dated May 31, 2021", 8 pgs.

CLOSURE ASSEMBLY THAT IS LATERALLY MOVABLE FOR SELECTIVE LOCKING

CROSS-REFERENCE TO RELATED APPLICATION

This application is a Continuation of U.S. patent application Ser. No. 15/941,128, filed on Mar. 30, 2018, the contents of which are incorporated herein by reference in their entirety.

FIELD

The present teachings relate to a device with a movable member and a ground member that are movable relative to each other and the device includes a movement unit and a latch unit that when connected prevent movement of the movable member and the ground member relative to each other, and specifically a closure assembly with a latch plate the is laterally movable between a lockable state and an unlockable state to selectively lock the closure assembly.

BACKGROUND

Generally, forceps may be utilized for laparoscopic surgery or open surgery. The forceps may be used to control delicate movements inside a patient. These forceps may be used to grip an anatomical feature. The forceps may include a gripping assembly or a cutting assembly. The forceps may include electrical energy for use in the gripping assembly, the cutting assembly, or both. The forceps have a pair of opposed resilient jaws that are closed against each other or a cutting blade. The jaws of the forceps may be locked together so that the surgeon may lock the forceps on a feature of interest while the surgeon works on a different anatomical feature or uses a different instrument. Examples of some latches or forceps including locks may be found in U.S. Pat. Nos. 5,104,397; 6,056,333; 6,247,733; 7,802,856; and 8,945,175 and U.S. Patent Application Publication No. 2013/0066317; 2014/0276795; 2015/0331443; 2016/0051275 all of which are incorporated by reference herein in their entirety for all purposes. During locking of the arms to each other the user may have to regrip one or more times in order to lock the jaws together. Furthermore, during releasing the user may be required to manipulate the jaws one or more times in order for the lock to release the jaws.

It would be attractive to have a device that is selectively movable between a lockable state and an unlockable state and a stop that prevents a movement unit from contacting a latch unit when the latch unit is in the unlockable state. What is needed is a latch plate that moves in a direction of a prescribed motion of a movement unit so that a distance between the latch plate and the movement unit is too large to lock the latch plate to the movement unit. What is needed is a latch plate that is movable both laterally and longitudinally. It would be attractive to have a latch plate that is longitudinally movable to expand and contract a bias member to assist in moving the latch unit between a locked state and an unlocked state or vice versa. What is needed is a closure assembly that has a small packing space, includes a closure assembly that entirely fits within a handle, or both.

SUMMARY

The disclosure meets one or more of the needs by providing: a closure assembly comprising a latch unit and a movement unit. The movement unit is connected to a movable member that moves along a prescribed path. The latch unit is connected to a ground member and the latch unit is movable relative to the ground member. The latch unit includes a latch plate that is movable between a lockable state and an unlockable state. The latch unit includes a stop that restricts movement of the movement unit relative to the hook latch.

The present teachings provide: a surgical device comprising: a closure assembly including: (a) a movement unit including: a bar that moves in a direction of a prescribed motion; (b) a latch unit including: (i) a latch plate including a hook latch that selectively receives the bar, the latch plate being movable in the direction of the prescribed motion between (A) a lockable state where the hook latch is engageable by the bar of the movement unit, and (B) an unlockable state where the bar does not reach the hook latch or the hook latch is moved out of alignment with the prescribed motion so that the hook latch is not engaged by the bar; and (ii) a stop that restricts movement of the movement unit relative to the hook latch.

The teachings herein provide a device that is selectively movable between a lockable state and an unlockable state and a stop that prevents a movement unit from contacting a latch unit when the latch unit is in the unlockable state. The teachings herein provide a latch plate that moves in a direction of a prescribed motion of a movement unit so that a distance between the latch plate and the movement unit is too large to lock the latch plate to the movement unit. The teachings herein provide a latch plate that is movable both laterally and longitudinally. The teachings herein provide a latch plate that is longitudinally movable to expand and contract a bias member to assist in moving the latch unit between a locked state and an unlocked state or vice versa. The present teachings provide a closure assembly that has a small packing space, includes a closure assembly that entirely fits within a handle, or both.

DETAILED DESCRIPTION

Figure 1:
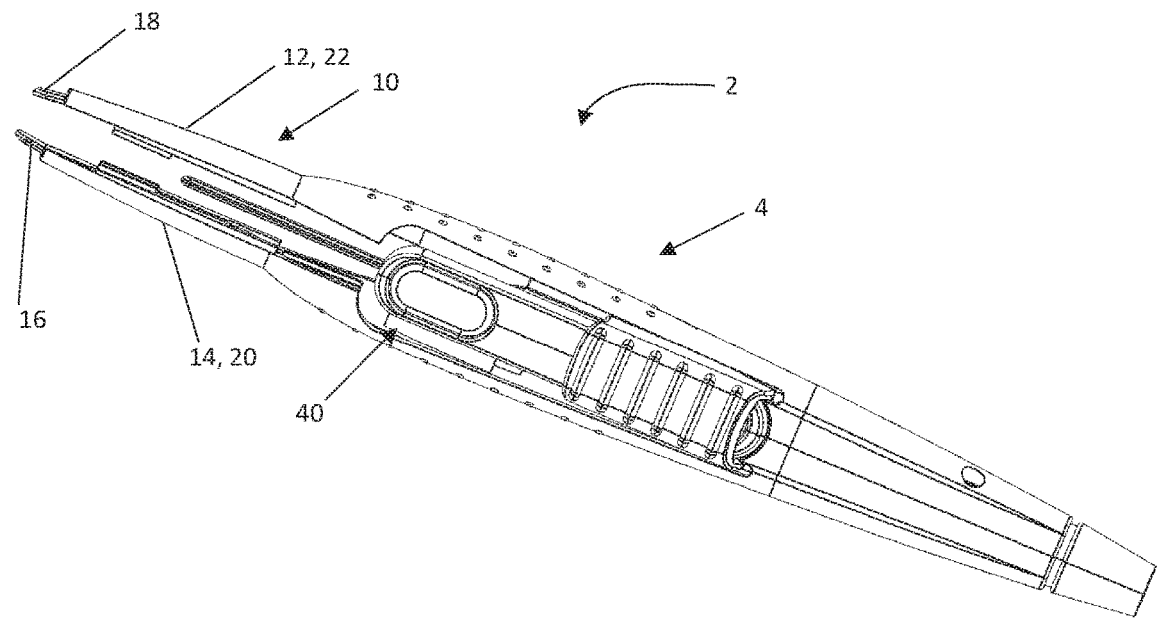
FIG. 1 is a perspective view of an electrosurgical device having a latching assembly.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to a closure assembly that connects two or more members together and prevents movement of the two members relative to each other. The closure assembly may connect a movable member to a ground member or connect two movable members together. The closure assembly may prevent movement of a door (e.g., movable member) relative to storage space (e.g., ground member). The closure assembly may be part of a hand-held device, pliers, clamps, or a combination thereof. The closure assembly may fit entirely within a hand piece, a housing, a handle, or a combination thereof that fits within a hand of a user. The closure assembly may move from a first side of a hand piece, a housing, a handle, or a combination thereof to a second side. The closure assembly may be part of a drawer, cabinet, bin, a door, or a combination thereof. Preferably, the closure assembly is part of a surgical device and prevents arms that control forceps from moving relative to each other.

The present teachings relate to a surgical device. The surgical device may be a non-electrical device (i.e., may only provide mechanical functions such as mechanical cutting or gripping). Preferably, the surgical device is an electrosurgical device. The electrosurgical device may provide one or more therapy currents. Preferably, the electrosurgical device provides two or more therapy currents (e.g., monopolar power and bipolar power). A therapy current may pass between the jaws (e.g., bipolar power). A therapy current may pass from a jaw to a blade or vice versa. A therapy current (e.g., monopolar power) may pass from a blade to a remote electrode (e.g., ground pad). The electrosurgical device may apply power before, after, or simultaneously with a mechanical technique (e.g., gripping or cutting). When power is applied an anatomical feature may be cut, cauterized, sealed, coagulated, or a combination thereof. The electrosurgical device may include a distal end and a proximal end. The distal end may include a portion of a forceps device (e.g., jaws, blade, or both). The distal end may be a portion of the surgical device that is farthest from a user. The proximal end may be a portion a user grips (e.g., hand piece or housing) or a portion closest to a user.

The present teachings provide a forceps device. The forceps may function to grip an object. Preferably, the forceps may be used during surgery to grip a feature of interest including: a part of a body, an anatomical feature, tissue, veins, arteries, or a combination thereof. The forceps may assist in applying a therapy current to a feature of interest. The forceps may move between a first position (e.g., release position) and a second position (e.g., gripping position). The forceps may be fully closed in a full-pull position or partially closed in a partial pull position. The forceps may function to be used in surgery, for example laparoscopic surgery. The forceps may be used with or without power. A therapy current may be passed from one jaw to a second jaw when tissue is located between the jaws and the therapy current may coagulate blood, cauterize, cut, or a combination thereof. In another example, a therapy current may be passed from one or more of the jaws and/or a blade to a remote electrode (e.g., a return pad). The forceps may include a first working arm with a jaw and a second working arm with a jaw. The forceps may be comprised of parts needed to perform the recited functions and may include generally, a stylet (e.g., a tubular member, a hollow tube, or an assembly of tubes), a hand piece, one or more operable mechanisms used to actuate the stylet, two or more jaws, two or more working arms, or a combination thereof.

The two or more working arms may function to move towards and away from each other to assist a user in gripping a feature of interest. The two or more working arms may be directly biased towards each other by a user. Preferably, the two or more working arms are biased towards each other by a stylet or tube moving over the arms (e.g., distally) so that the arms are moved together. The two or more working arms may be moved towards each other by being retracted into a stylet or tube. The working arms may be solid and rotate about a pivot. The working arms may be a wire that is shaped to create a working arm, a jaw, or both. The working arms may have one or more rods, one or more wires, or both that extend into a stylet and connect to the hand piece. Each of the two or more working arms may include a jaw.

The two or more opposing jaws may function to create a gripping force, grip a feature of interest, or both. The two or more opposing jaws may move towards each other to create a gripping force, to grip a feature of interest, or both. The two or more opposing jaws may function to be used to grip or clamp an item of interest for cutting or applying a bipolar energy source. Preferably, the two or more opposing jaws may be one jaw structure with another mirror image opposing jaw structure (i.e., identical) that when forced together may create a gripping function. The two opposing jaws may be any two or more structures that may be movable relative to each other for perform a gripping function. The two opposing jaws may be any structures that may allow one jaw to be static and one jaw to be movable or any combination thereof. The jaws may be a gripping portion of a working arm. The two opposing jaws may be formed of two wires that are shaped to have a generally "U" shaped end. The two opposing jaws may be made of any material so that the two opposing jaws may be used to create a gripping force. The two opposing jaws may be made of a flexible material, resilient material, rigid stainless steel, a plastically deformable material, an elastically deformable material, or a combination thereof. The two opposing jaws may be made of a material that conducts electricity. The two opposing jaws may include a channel (e.g., a blade track) to allow for a cutting instrument to be inserted while retaining functionality of the two or more opposing jaws.

The two opposing jaws may be used to apply electricity to a feature of interest that may be gripped by the two opposing jaws. The two opposing jaws may be a first jaw and a second jaw. The first jaw may be movable relative to the second jaw, or vice versa. The first jaw and second jaw may be longitudinally movable relative to each other. Preferably, the first jaw and second jaw longitudinally move in unison. The first jaw and second jaw may be longitudinally static. The first jaw and second jaw may move about a pivot towards and away from each other. The two opposing jaws may be moved between a release position and a retract position by retraction of one of the one or more jaw shafts, movement of the one or more tubular members towards the distal end, or both along an axis of the one or more tubular members; an application of force by a user; or a combination thereof. The two opposing jaws may have laterally extending arcuate sections at the proximal end (e.g., heel of the jaw) of the jaws that protrude out from the distal end of the tubular member, while one or more jaw support rods extend into the tubular member. A closure assembly may lock the two opposing jaws together, lock the two opposing jaws on tissue, lock the two opposing jaws on a blade, or a combination thereof.

The blade may function to cut a feature of interest. The blade may be any cutting tool that may be used in surgery, for example laparoscopic surgery or open surgery. The blade may be any cutting device that may be extended and retracted through the stylet or between the first working arm and the second working arm. The blade may extend along a stylet. The blade may be made of any material that may be sharpened; is strong enough to cut a feature of interest; is biocompatible; that may conduct electricity; or a combination thereof. The blade may mechanically cut, electrically cut, or both. The blade may be substantially solid along a length of the blade. The blade may be sufficiently small so that the blade may be housed in the tubular member, tube, or both of a stylet during movement, insertion, or both. The blade may be extended into, and retracted from, the channel in the two opposing jaws. The distal end of the blade may have a shaped edge (e.g., sharpened). The blade may extend flush with or distal of the jaws. The blade may conduct power. The blade may conduct a therapy current. The blade may conduct bipolar energy, monopolar energy, or both. The proximal end of the blade may be attached to a blade support rod. All or a portion of the blade may extend out of the stylet, between and past the jaws, or both to cut a feature of interest.

The stylet as discussed herein may include one or more tubular members or may be a tubular member (i.e., tube). The stylet may be a neck that connects jaws, a blade, or both to a hand piece. The stylet may have a hollow cross-section, a solid cross-section, or both. The stylet may include one or more tubes, one or more shafts, or both that may extend through the tubes. The stylet may include a tubular member and an inner tube. The stylet may include a tube that extends around all or a portion of an inner tube. The stylet may be a hollow tube with one or more shafts extending through the hollow tube. The stylet may function to extend into a patient during a surgical procedure so that a user (i.e., surgeon) can perform one or more surgical procedures. The stylet may be flexible so that the stylet may be moved within a patient. Preferably, the stylet may be substantially rigid so that the stylet may be moved to a desired location. The stylet includes a distal end and a proximal end. The distal end may be an end of the stylet that is located farthest from the hand piece (e.g., the end of the stylet that is inserted into a patient). The proximal end of the stylet may be the end of the tube located proximate to the user, in the hand piece, or both. The stylet and its components may be made of any biocompatible material, for example, stainless steel, plastic, a synthetic material, a natural material, or a combination thereof. The tube sub-assembly may include one or more tubes, one or more inner tubes, one or more outer tubes, one or more gripping assemblies, one or more cutting assemblies, one or more rotation mechanisms, one or more operable mechanisms, one or more camming shafts, one or more guides, one or more spacing members, one or more jaw shafts, one or more blade shafts, or a combination thereof. Preferably, the stylet includes at least an outer tube that extend from a hand piece to a distal end.

The one or more outer tubes may function to close the jaws, bias the jaws, or both. The one or more outer tubes may function to house one or more jaws, one or more blades, or both. The one or more outer tubes may be axially static. The one or more outer tubes may axially move to open and close the jaws. The one or more jaws may move relative to the inner tube. The one or more jaws may overrun the inner tube, the jaws, the arcuate sections, or a combination thereof to bias the jaws towards each other. The one or more inner tubes may function to create a point of contact for one or more jaws. The one or more inner tubes may form a connection point, include a connection feature (e.g., a pin, bolt, screw, rivet, or a combination thereof) for one or more jaws. The one or more inner tubes may connect to a pivot joint of one or more jaws so that the one or more jaws rotate about an axis. The one or more inner tubes may be located distal of one or more tubes. The one or more inner tubes may be part of a tubular member or a stylet. The one or more inner tubes may be movable relative to an outer tube. The one or more inner tubes may be axially movable, rotationally movable, or both relative to an outer tube, a camming shaft, or both. The one or more inner tubes may be static and an outer tube may be movable relative to the inner tube. The one or more forceps may be free of any tubes or tubular members. The one or more inner tubes, outer tubes, stylets, or a combination thereof may form part of a fluid distribution system, connect a fluid distribution system between a jaw, blade, or both and a hand piece. The one outer tubes of the stylet may assist in connecting the jaws, the blade, or both to the hand piece.

The hand piece may be an assembly of parts or housing structures capable of forming a structure with a cavity that a user holds in their hand. The hand piece may function to be gripped by a user. When gripped by a user a top or upper portion of the handpiece may be located up relative to a user's hand and the bottom or lower portion may be located down relative to a user's hand. Thus, up may include the one or more button, a region the stylet extends from, or both, and down may be where a cord extends out of the hand piece. The hand piece may function to hold or encapsulate one or more or a plurality of components of the surgical device. The forceps may extend from the hand piece and may be actuated by one or more operable mechanisms located within the hand piece. The forceps may be actuated by direct pressure being applied to one or both of the jaws that extend from the hand piece so that the jaws are moved towards or away from each other (e.g., laterally moved). The forceps may be actuated by movement of a trigger that is connected to the hand piece. The hand piece and the trigger may be biased apart. A bias device may extend between the hand piece and the trigger so that a gap is located between the hand piece and the trigger. The hand piece and the trigger may be biased apart. A bias device may extend between the hand piece and the trigger so that a gap is located between the hand piece and the trigger. A bias device may be located along the stylet, within the hand piece, in communication with a part that axially moves so that the working arms are moved together, or a combination thereof. The bias device may be a bias device taught herein including those taught in U.S. Pat. No. 9,851,741 regarding a compression spring or element 90 or the teachings of U.S. Pat. No. 5,735,849 regarding a torsion spring or element 80 the teachings of which are incorporated by reference herein for all purposes include those regarding how a moveable member is moved relative to a ground member and especially how a trigger is moved relative to a handle. The hand piece may be solid and the first working arm and the second working arm, the first jaw and the second jaw, or both may be biased apart by a bias member. The hand piece may include the latch unit and the trigger may include the movement unit and when the movement unit and the latch unit are not connected together the bias member may move the trigger to form the gap therebetween. A first working arm may include the latch unit and a second working arm may include the movement unit. The forceps may create a sufficient gripping force so that one or more features of interest (e.g., a patient's body) may be manipulated by the gripping assembly, secured by the gripping assembly, or a combination thereof. The forceps may grip and release while being simultaneously rotated about the hand piece. The forceps may be actuated by the actuation mechanism in communication with the forceps or a user directly contacting the forceps. The hand piece may function to form an enclosing structure for all or a portion of the forceps, a gripping portion for the user, a main portion for manipulating the forceps, or a combination thereof. The hand piece may be any device that houses all or a portion of the working assemblies and parts of the forceps. The hand piece may be comprised of one or more housing structures. Preferably, the hand piece is two or more housing structures. The housing structures may be two plastic pieces that connect together to enclose an open space that receives components of the surgical device. The hand piece may be any structure that is gripped by a user. The hand piece may be a ground member. The hand piece may be static. The hand piece may be a ground member that is static when a user applies a pressure to so that a movable member is moved relative to the ground member. The hand piece may assist in performing laparoscopic surgery. The hand piece may be ergonomically shaped. The hand piece may be used ambidextrously. The housing structures may form a cavity to house working assemblies of the forceps. The housing structures may be one or more housing structures and preferably two or more housing structures. The housing structures may be any device that includes a recess for receiving one or more components of the forceps. The housing structures may house all or a portion of one or more operable mechanisms, one or more valves, one or more fluid distribution systems, or a combination thereof. The housing structure may house all or a portion of an operable mechanism that causes the jaws to move, the blade to move, the valve to open, the valve to close, all or a portion of a fluid distribution system, or a combination thereof. The housing structure may be made of one or more housings.

The one or more housings may function to form a hand piece, enclose a portion of an operable mechanism, enclose a portion of a stylet, enclose one or more tubes, or a combination thereof. The one or more housings may be a left half and a right half. The housing may be multiple pieces that are connected together. The housing may be made of plastic. The housing may be a combination of plastic and metal. The housing may provide a stationary part (e.g., ground member) that a user grips while a user moves a trigger (e.g., movable member) to actuate the forceps, a blade, or both. Preferably, the housing is connected to two or more triggers that movably connect to the housing so that upon actuation the jaws, blade, fluid distribution system, or a combination thereof are moved or actuated by one of the two or more triggers. More preferably, the triggers are movable relative to the housing to actuate the jaws, blade, fluid distribution system, or a combination thereof. The housing may be connected to a first jaw, a second jaw, or both jaws of forceps and a direct force may be applied to the housings in order to move the forceps towards or apart from each other. For example, upon a force being applied to the housing the jaws may move towards each other. In another example, upon a force being applied to the housing the jaws may move apart. The housing may be a proximal end (e.g., end closest to a user) and the jaws or blade may be the distal end (e.g., end farthest from a user). The jaws, blade, fluid distribution system, or a combination thereof may be moved between a first position (release position) and a second position (retract position) by one or more operable mechanism or direct contact by a user. The housing may have a portion that is a handle that a user grips.

The handle may function to assist in actuation of the forceps, the blade, applying electricity, or a combination thereof. The handle may be gripped by one hand. The handle may be part of the hand piece. The handle may include a lock, a lock plate, all or a portion of a closure assembly, a latch unit, or a combination thereof. The handle may be a proximal end of the surgical device. The handle may extend from a body portion or the hand piece. The handle may extend from an angle relative to the body portion of the hand piece. The handle may be a static member that one or more triggers move relative to. The handle may be a ground member that a movable member, a trigger, or both are movable relative to.

The ground member may function to be static and another part (e.g., the movable member) may be moved relative to the ground member. The ground member may form a coordinate system, a reference point for relative motion of other components of the device taught herein, or a center of a coordinate system. The ground member may be connected to or located next to a movable member and function to prevent movement of another component such as forceps or a blade as the movable member moves relative to the ground member. The ground member may be part of a first working arm. The ground member may be a handle, a housing, a hand piece, a trigger, a jaw, or a combination thereof. Preferably, the ground member is the handle or hand piece. The ground member may include all or a portion of a closure assembly. The ground member may include all of the latch unit. The ground member may receive a portion of a force to assist a movable member in being moved relative to the ground member. The ground member may receive a portion of the movable member to form a locked state.

The movable member may function to move relative to a ground member so that the forceps or blade may be actuated, locked, released, or a combination thereof. The movable member may be biased apart from the ground member (e.g., a bias device may be located between the movable member and the ground member). The movable member may move with or relative to a ground member to lock, unlock, bias, or a combination thereof two or more jaws two or more working arms, a blade, or a combination thereof. The movable member may move to open and close the jaws, move the blade, or both. The movable member may be a trigger. The movable member may be a cut trigger, a clamp trigger, or both. The movable member may include all or a portion of the closure assembly. The movable member may include the movement unit. The movable member may rotate about a pivot so that the movement unit moves along movement path (e.g., prescribed motion). The movable member may be part of the closure assembly that assists in locking the jaws, the working arms, the surgical device, or a combination thereof.

The closure assembly may function to connect a movable member and a ground member together. The closure assembly may function to lock a first working arm to a second working arm, a first jaw to a second jaw, a blade in an extended state or in a retraced state, or a combination thereof. The closure assembly may be movable between a lockable state and an unlockable state. The closure assembly may lock two items together when the closure assembly is in a locked state. The closure assembly may freely move as the movable member, the ground member, or both move relative to each other or are in an unlockable state. A portion of the closure assembly may be located on or within the movable member, the ground member, the movement unit, the latch unit, or a combination thereof. Preferably, the closure assembly includes a movement unit and a latch unit. More preferably, the closure assembly may be part of a movable member and a ground member and the movable member may be a trigger and the ground member may be a handle.

The one or more triggers function to be an input to an operable mechanism that moves one or both jaws, one or both working arms, one or more blades, or a combination thereof. The one or more triggers may function to be an input that directly moves one or more working arms, a blade, or both. The one or more triggers may be a movable member or a ground member. Preferably, the triggers are a movable member and the ground is a handle or hand piece. The one or more triggers as discussed herein may be a lever, handle, link, or a combination thereof. The one or more triggers may be a cut trigger, a clamp trigger, an activation switch, or a combination thereof that when actuated inputs movement into an operable mechanism so that the operable mechanism provides an output. If the triggers are a lever, the lever is a rigid member that turns on a pivot. The cut lever, the clamp lever, or both may function to move one or more jaws, one or more blades, a jaw support rod, a blade support rod, a second link, one or more valves, or a combination thereof. The cut lever, the clamp lever, or both may extend between a release position (e.g., a start position) and a retract position (e.g., a full pull position where the jaws are closed, the blade is extended, or both). The cut lever and the clamp lever may be individually biased apart from the handle, the hand piece, or both. The cut lever, the clamp lever, or both as they extend from a start position (or home position) to a full pull-position may close jaws, activate a functional element, extend a blade, or a combination thereof. For example, as the clamp trigger is moved, the clamp trigger may begin to close the jaws and as the jaws close a closure assembly may simultaneously be closed such that the jaws are locked together. The one or more triggers may be part of the closure assembly, part of a movement unit, or both. Preferably, the one or more triggers carry the movement unit so that the movement unit when in communication with the latch unit may restrict movement of the trigger.

The movement unit may be integrally connected to a movable member, a trigger, or both. The movement unit may extend from the movable member towards the ground member and even into the ground member. The movement unit may move in a prescribed motion. The prescribed movement may be a linear motion, an arcuate movement, or a combination of both. The prescribed motion may overlap in a first direction and a second direction. For example, the bar extending along the prescribed motion in a forward stroke is the same movement location when the bar extends along the prescribed motion in the return stroke. The movement unit may rotate about a pivot so that the movement unit travels back and forth along a constant path (e.g., a prescribed motion). The movement unit may extend cantilever from a movable member, a trigger, or both. The movement unit may extend into contact with a latch unit to form a locked state. The movement unit may move in relationship to the latch unit to form an unlocked state. The movement unit may move in a prescribed motion at all times and the latch unit may move relative to the movement unit so that a lockable state, an unlockable state, a locked state, an unlocked state, or a combination thereof may be formed. The movement unit may include one or more bar arms, one or more bars, or both.

The one or more bar arms may function to extend from a movable member so that a portion of the bar arm, the bar, or a combination thereof are extendable into a ground member, a latch unit, or both. The one or more bar arms may extend cantilever from the trigger, the movable member, or both. The one or more bar arms may extend partially into the latch unit, a latching pathway, around a hook latch, or a combination thereof. The one or more bar arms may be located at virtually any location on a movable member, a trigger, or both. Preferably, the one or more bar arms are located on a bottom of the movable member. The one or more bar arms may be linear in shape. The one or more bar arms may be tapered. The one or more bar arms may taper as the bar arms extend away from the movable member and towards the ground member. The one or more bar arms may taper in shape so that once a sufficient amount of the bar arm extends into the latch unit, the latching pathway, or both the one or more bar arms may be prevented from extending further into the latch unit, the latching pathway, or both. A distal end, narrowest region, tapered portion, end that extends into the latch unit, end that extends into the latching pathway, or a combination thereof may include one or more bars. Preferably, the one or more bars may be located on a side of the bar arm. More preferably, the one or more bars extend substantially normal from the bar arm.

The one or more bars may function to connect the movement unit to the latch unit so that movement of the movable member relative to the ground member is prevented (e.g., create a locked state). The one or more bars may move through a pathway to connect and release a closure assembly. Preferably, the one or more bars connect a movement unit to a latch unit. More preferably, the one or more bars connect to the hook latch to form a locked state. The one or more bars may be virtually any shape so that the bars are movable through a latching pathway into the latch unit and then along a pathway to create a locked state and an unlocked state. The one or more bars may contact a hook latch to create a locked state. The one or more bars may be moved away from a hook latch to move along the pathway from a locked state to an unlocked state. The one or more bars may only extend along one side of the hook latch. Preferably, the one or more bars may circumnavigate the hook latch. The one or more bars may be a projection that extends from the bar arm and ultimately from a movable member or a trigger so that when the bar is trapped the movable member, the trigger, or both are prevented from being moved. The bar may be cylindrical, cubical, a cone, a cuboid, or a combination thereof. Preferably, the bar is cylindrical so that the bar may extend through a latching pathway, into the latch unit, and around a pathway of the latch unit.

The latching pathway may function to receive the bar into the latch unit, the ground member, the housing, the handpiece, the handle, or a combination thereof. The latching pathway may be an opening in the housing, hand piece, forceps, handle, or a combination thereof. The latching pathway is aligned within bar so that as the bar moves in a prescribed motion the bar will pass into and through the latching pathway. The latching pathway may be an absence of material. The latching pathway may be part of the housing, handle, hand piece, or a combination thereof (e.g., a gap or spaced formed in the housing). The latching pathway may have one or more depths. The latching pathway may be an internal structure or an external structure. The latching pathway may permit the bar to extend through a portion (e.g., the bar pathway). The latching pathway may permit a portion of the bar arm to extend into the latching unit, the handle, or both (e.g., bar arm pathway). The latching pathway may have a height, width, length, or a combination thereof that permits a locking arm to extend a predetermined distance along the prescribed motion of the movable member. The bar arm pathway may be longer than the bar pathway. The bar pathway may have a thickness that is less than the bar pathway. The bar may not fit through the bar arm pathway. The bar arm pathway may contact a portion of the bar arm to restrict movement of the movable member. The bar pathway may be a deeper portion of the bar arm pathway where the bar can extend through into the latch unit. The latching pathway may permit ingress and egress of the latch unit relative to the housing, the handle, hand piece, a stop, a trigger stop, an aperture, or a combination thereof. Preferably, the latching pathway is located internal of an aperture.

The one or more apertures may function to protect a latching pathway, create a stop, create a trigger stop, form an opening in an external wall of the housing, or a combination thereof. The one or more apertures may be an opening in the hand piece, housing, handle, or a combination thereof. The aperture may permit the movement unit to extend into the latch unit. The aperture may restrict movement of the movement unit relative to the latch unit. The aperture may create a trigger stop that contacts the movable member, a trigger, the cut trigger, the clamp trigger, or a combination thereof. For example, the aperture may be a trigger stop when only a predetermined amount of a trigger may extend into the aperture before the aperture contacts the trigger to restrict movement.

The trigger stop may function to restrict motion of a movable member, trigger, of both relative to a ground member, a handle, or both. The trigger stop may restrict movement of the movement unit relative to latch unit. The trigger stop may restrict movement of a bar along the prescribed path. The latching pathway may extend through the trigger stop. The trigger stop may be an outer wall of the hand piece, the handle, the housing, or a combination thereof. The trigger stop may be an inner portion of the latching pathway where the bar arm contacts so that movement is prevented. The trigger stop may be located at any location along the movable member, the ground member, or both. Preferably, the trigger stop is part of the ground member, handle, or both. The trigger stop may be flush with the trigger, the movable member, the ground member, the handle, or a combination thereof. The trigger stop may extend outward from the trigger, the movable member, the ground member, the handle, or a combination thereof. The trigger stop may be an internal wall located within the hand piece that contacts a portion of the bar arm as the bar arm travels along a prescribed motion. The trigger stop may allow the bar to contact the latch unit when the latch unit is in the lockable state and to prevent the bar from contacting all or a portion of the latch unit when the latch unit is in the unlockable state. The trigger stop may be located on the handle or the trigger and restrict movement of the trigger relative to the handle so that when the hook latch, latch unit, or both are in the unlockable state the handle bottoms out before the bar reaches the entry apex, extends around the entry apex, or both. The trigger stop may prevent a trigger from extending a sufficient distance to create a locked state when the latch unit is in the unlockable state.

The latch unit may function to create a connection with a movement unit so that the movable member and the ground member are locked together. The latch unit may retain a portion of the movement unit. The latch unit may move as the movement unit moves along a prescribed path, an arcuate movement, or both. For example, as the movement unit moves along the prescribed path the movement unit may move the latch unit so that the latch unit and the movement unit are moved into a locked state, an unlocked state, or both. The latch unit may include a lockable state, an unlockable state, or both. The latch unit may be under a load (or pre-load) when the closure assembly is moved between or to a home position, a locked position, an unlocked position, a lockable state, an unlockable state, or a combination thereof. Preferably, the latch unit is free of a load when the latch unit is in the home position, the latch unit is free of contact with the movement unit, or both. The latch unit may move along a longitudinal axis (e.g., all or a portion of the latch unit may move along the handle, the hand piece or both up and down as the movement unit moves into contact with the hook latch or out of contact with the hook latch). The all or a portion of the latch unit may move along a length of the handle. The latch unit may include one part. The latch unit may include one movable part. The latch unit may include one unitary part that includes a bias member, a latch plate, hook latch, adjustment switch, and guide aperture. Preferably, the latch unit includes a latch plate. More preferably, the latch unit is a single piece. The latch unit may be constrained within the handle by a sidewall, a forward stop, a backward stop, an adjustment switch, a selection plate, a compression stop, a connection pin, a guide aperture, or a combination thereof.

The sidewall may function to restrict movement of the latch unit, the latch plate, or both. The sidewall may restrict forward movement, rearward movement, downward movement, upward movement, or a combination thereof. The sidewall may extend along all or a portion of the latch unit, the latch plate, or both. The sidewall may be part of the housing, the handle, the hand piece, or a combination thereof. The sidewall may restrict the latch unit so that the latch unit moves longitudinally relative to the handle. The sidewall may permit longitudinal movement but may restrict lateral movement. The sidewall may be an internal wall within the housing, the handle, the hand piece, or a combination thereof. The sidewall may have an external portion and an internal portion. The sidewall may be a trigger stop, a forward stop, a backward stop, a compression stop, or a combination thereof.

The forward stop may function to restrict lateral movement of the latch plate, stop the latch plate in a lockable state, or both. The forward stop may align the hook latch, the latch plate, or both with a latching pathway. The forward stop may prevent motion of the hook latch so that hook latch at a distance where the latch unit and the movement unit are connected together. The forward stop may include all or a portion of the latching pathway. The forward stop may be an internal wall. The forward stop may be an external wall. The forward stop may contact any portion of the latch plate so that lateral movement (e.g., in a direction parallel to the prescribed movement) of the latch plate is restricted or stopped. For example, the forward stop is located in a handle by the trigger and a backward stop is located on an opposite wall of the handle and the lateral movement is between the forward stop and the backward stop. The forward stop may restrict or prevent movement of the latch plate in a direction that is substantially perpendicular to the longitudinal axis of the handle, the latch plate, or both (e.g., within about 10 degrees or less, or about 5 degrees or less). The forward stop may include the latching pathway. The forward stop may be substantially parallel to the backward stop.

The backward stop may function to restrict lateral movement of the latch plate, stop the latch plate in an unlockable state, or both. The backward stop may stop the latch plate a distance from the latching pathway so that the movement unit, the bar, or both cannot extend into contact with the latch plate to create a locked state. The backward stop may misalign the hook latch, the latch plate, or both with the latching pathway. Preferably, the backward stop is located a sufficient distance from the forward stop so that when the latch plate is in contact with the backward stop the bar cannot lock. More preferably, when the latch plate is in contact with the backward stop the bar cannot extend around an entry apex into the pocket. The rearward stop may be an internal wall. The rearward stop may be external wall. The rearward stop may contact any portion of the latch plate so that lateral movement of the latch plate is restricted or stopped. The rearward stop may restrict or prevent movement of the latch plate in a direction that is substantially perpendicular to the longitudinal axis of the handle, the latch plate, or both (e.g., within about 10 degrees or less, or about 5 degrees or less). The forward stop and the backward stop may prevent movement of the latch plate as the latch plate pivots about a connection pin.

The one or more connection pins function to connect the latch plate within the latch unit. The one or more connection pins may function to guide the latch plate and assist in rotational movement of the latch plate. The one or more connection pins function to retain the latch plate within the handle while allowing the latch plate to rotate, laterally move, longitudinally move, or a combination thereof. The one or more connection pins may function to assist the latch plate in moving between a lockable state and an unlockable state. The one or more connection pins may function to restrict movement of the latch plate. The one or more connection pins may guide the latch plate in the longitudinal direction. The one or more connection pins may be part of the handle, the hand piece, the housing, or a combination thereof. Preferably, the connection pins are a single pin. The one or more connection pins may restrict movement of the latch plate in a first direction, a second direction, or both. The one or more connection pins may ground the latch plate to the handle, the housing, the hand piece, or a combination thereof. The one or more connection pins may be connected to and extend from the latch plate into a guide aperture in the housing, handle, hand piece, or a combination thereof. The one or more connection pins may extend through a guide aperture.

The one or more guide apertures may function to receive a connection pin, permit rotational movement of the latch plate, permit longitudinal movement of the latch plate, permit lateral movement of the latch plate, or a combination thereof. The one or more guide apertures function to guide the latch plate. The guide apertures may guide the latch plate in moving between a lockable state and an unlockable state. The one or more guide apertures may be moved into contact with the connection pins as the latch plate longitudinally moves, rotationally moves, laterally moves, or a combination thereof. The one or more guide apertures may have a cross-sectional thickness (e.g., width or diameter) that is substantially the same size as the cross-sectional thickness (e.g., width or diameter) of the connection pins so that the latch plate moves along the longitudinal axis of the handle, the latch plate, or both. The guide apertures may be oval, round, have flat walls, have rounded ends, or a combination thereof. Preferably, the guide aperture is an elongated slot. The guide aperture may allow a connection pin to travel to lock the closure assembly. The guide aperture may be similarly sized to the connection pin so that the communication between the guide aperture and the connection pin restrict movement of the latch plate. A length of the guide aperture may determine an amount of movement of the latch plate. The length of the guide aperture allows movement of the hook latch from the home position. The guide apertures may allow the bias member to expand and contract, elastically deform, or both. The guide apertures may restrict movement of a first end as the second end pivots between a lockable state and an unlockable state. The one or more guide apertures may be part of the latch plate, the handle, the hand piece, the housing, or a combination thereof. The one or more guide apertures may contact a connection pin to restrict movement of towards a compression stop, away from a compression stop, or both.

The compression stop may function to prevent the bias member, the latch plate, or both from moving in a direction, from exiting the hand piece, exiting the handle, exiting the housing, or a combination thereof. The one or more compression stops may restrict movement of one end of the bias member, the latch plate, or both. The one or more compression stops may function to retain an end of the bias member, the latch plate, or both so that the bias member may be elongated, loaded, or both. The one or more compression stops may assist in compressing the bias member form a home position to a compressed position so that energy, a load, or both is stored within the bias member. The one or more compression stops may be an internal wall or an external wall of the handle, the housing, the hand piece, or a combination thereof. The compression stop may have an aperture that extends along the switch path. The compression stop may allow the latch plate to move along the switch path between a lockable state and an unlockable state. The one or more compression stops may retain the selection plate, adjustment switch, or both from longitudinally moving but permit the selection plate to laterally move, rotationally move, or both.

The selection plate may function to change the closure assembly between a lockable state and an unlockable state. The selection plate may move along a sliding axis, a switch path, or both to activate and deactivate the closure assembly (e.g., change the latch unit between a lockable state and an unlockable state). The selection plate may allow a user to enable and disable the closure assembly. The selection plate may be substantially entirely located within the housing, hand piece, handle, or a combination thereof. The selection plate may be connected to the bias member, the latch plate, or both. The selection plate may have a portion located inside of the compression stop, a portion that extends through the compression stop, and a portion that extends outside of the compression stop. The selection plate may include an adjustment switch that extends out of the housing, hand piece, handle, or a combination thereof to permit movement by the user.

The adjustment switch may function to move the closure assembly, deactivate the closure assembly, activate the closure assembly, or a combination thereof. The adjustment switch may be exposed so that upon a force being applied to the adjustment switch the state of the closure assembly is changed. The adjustment switch may be a thumb switch. The adjustment switch may include one or more gripping portions. The adjustment switch may contact the walls of the housing as the selection plate moves so that a longitudinal distance of movement of the selection plate is restricted. The adjustment switch may be movable along a switch path. The switch path may be parallel to the sliding axis. Preferably, the switch path is perpendicular to the longitudinal axis of the handle, the latch plate, or both. The switch path and the sliding axis may be coplanar. The adjustment switch may move the selection plate so that the latch plate is moved between the unlockable state and the lockable state to change the function of the closure assembly (e.g., activate and deactivate).

The unlockable state detent functions to allow free movement of the movable member and the ground member relative to each other by locking the position of the latch unit out of the path of the movement unit or a distance from the movement unit so that the movement unit cannot lock to the ground unit. For example, when the selection plate is moved to be locked at the unlockable state detent the triggers may freely move relative to the hand piece, the handle, the housing, or a combination thereof. The unlockable state detent functions to lock the latch plate, the hook latch, or both out of alignment with or out of reach from the bar, the closure assembly, or both so that a lockable state is not created. The lockable state detent functions to restrict movement of the movable member and the ground member relative to each other by locking the position of the latch unit, the latch plate, the hook latch, or a combination thereof in the path of the movement unit. The unlockable state detent function to move the latch plate, the hook latch, or both a distance away from the bar so that the bar cannot reach the hook latch to create a locked state. The unlockable state detent and the lockable state detent (hereinafter detents) may lock the selection plate, the latch plate, or both in a lockable state or an unlockable state. The detents may allow a user to select if the closure assembly is activated. The detents may allow a user to laterally move or rotationally move the adjustment switch between positions and lock the adjustment switch is a desired state. The detents may be a recess that receives a pin or a pin that extends into a recess. The detents may prevent movement once a state is selected. The detents may be located within the housing, on the handle, on the hand piece, or a combination thereof. Preferably, the handle, the housing, the hand piece, or a combination thereof include two or more detents. The detents may positively receive a detent pin. The detents may be sinusoidal in shape. The detents may have two or more valleys and each valley may be separated by a peak. Preferably, the detents include at least three peaks with a valley between the three peaks forming a lockable state detent and an unlockable state detent. Once the pin gets over the peak the pin may fall into a valley and lock. More preferably, the detents are a recess or valley located in the housing, handle, hand piece, or a combination thereof. The detents may assist in moving a pin into a locked state once the pin receives a predetermined point and if the pin does not reach the predetermined state then the pin returns to another detent until a stable state is obtained.

The detent pin functions to create a locked state, an unlocked state, or both with the closure assembly. The detent pin functions to contact a detent and then lock the latch plate in a selected location. The detent pin may be a projection that extends into and is received by the detent. The detent pin may flex as the detent pin moves from one detent to another detent. The detent pin may be connected to the bias member. The bias member may flex to allow the detent pin to move between the lockable state and the unlockable state. The detent pin may be a pawl. The bias member may create a force that pushes the detent pin to the unlockable state detent, the lockable state detent, or both. The bias member that biases the detent pin may be the same bias member that biases the hook latch. The detent pin may be static and the detents may flex during movement of the selection plate. The detent pin when located within a detent the detent may restrict movement of the latch plate until a user acts upon an adjustment switch. The detent pin may be part of the housing, the handle, the hand piece, bias member, or a combination thereof. The detent pin may ground (e.g., prevent movement of) the closure assembly, the latch unit, the latch plate, or a combination thereof. The one or more detents may act as a stop; however, the closure assembly may include a rear stop, a forward stop, or both to constrain movement of the selection plate relative to the latch plate or vice versa.

The one or more latch plates may function to move when a hook latch is contacted by a bar so that a locked state, an unlocked state, or both are created. The latch plate may carry one or more elements that form the pathway (e.g., a path that a bar moves along as the bar moves from a locked state to an unlocked state). The latch plate may carry or include the bias member, detent pin, the hook latch, the wall guide, guide aperture, connection pin, selection plate, adjustment switch, or a combination thereof. Preferably, the latch plate is an integral piece that includes the bias member having a detent pin and an adjustment switch, a selection plate including a hook latch, wall guide, and guide aperture. The latch plate may rest in a home state and then movable once acted upon by the movement unit. The latch plate may only move or be movable when the latch unit is in a lockable state (e.g., during locking or unlocking of the closure assembly or moving the closure assembly between a lockable state and an unlockable state). The latch plate may only move when biased by the movement unit. The latch plate may move along the prescribed motion between the lockable state and the unlockable state. All or a portion of the latch plate may move in the direction of the prescribed motion, along the prescribed motion, or both between a first state (e.g., lockable state) and a second state (e.g., unlockable state). The latch plate may include one or more detents, a detent pin, or both that assist in locking the latch plate in each state (e.g., the unlockable state, the lockable state, or both). The latch plate may move along the sliding axis, tracks, the hand piece, the housing, or a combination thereof. The latch plate may move in a longitudinal direction, along a longitudinal axis, or both of the hand piece, the handle, the latch plate, or a combination thereof (e.g., the latch plate path). The latch plate path may be a longitudinal movement of the latch plate up and down, toward and away from the home position, or both. Preferably, the latch plate path extends along the prescribed motion of the bar. The latch plate may move between a forward stop and a rearward stop in the housing along a latch plate path. The latch plate may longitudinally move as a bias member expands, contracts, or both.

The bias member may function to store energy when a force is applied to the latch plate and then to release the energy when the force is removed. The bias member may function to move the latch plate to a home position. The bias member may assist in locking or unlocking the movable member and the ground member. The bias member may be any material that may store energy. The bias member may be a double acting member. For example, a load of the bias member may be increased in a first direction and increased in a second direction. The home position may be a zero load state or zero energy state. The first direction and the second direction may be relative to the home position. The biasing member may act upon the housing, the hook latch, or both. The bias member may be a dual acting member that acts on two members simultaneously. The bias member may be free of a load when the bias member is in a home position. The bias member may be elastomeric, rubber, a spring steel, helical, round, cylindrical, or a combination thereof. The bias member may be a piece of rubber that is compressible, expandable, or both. Preferably, the bias member is a dual acting bias member. More preferably, the bias member is a deformable body that includes a plurality of elastically deformable connections. The plurality of elastically deformable connections may be connected to each other, movable relative to each other, or both to store and release energy. The plurality of elastically deformable connections may be serpentine in shape, switch back and forth, be a plurality of "U" shaped members connected together, be a plurality of "C" shaped members connected together, or a combination hereof. The bias member, the plurality of elastically deformable connections, or both may be elastically deformable. Preferably, the bias member is not a spring, helically wrapped, or both. The biasing member may provide a bias between the hook latch and the housing. The bias member when located within the latch unit and the latch unit being in a home position may be free of any load. The bias member when expanded, contracted, or both may have a load. The bias member may increase in load as the bias member moves away from latch plate moves away from the home position. A load on the bias member may be increased when the latch unit moves in a first direction, a second direction, or both relative to a home position of the latch unit. An increase in load or a change in load may be about 1 N or more, about 3 N or more, about 5 N or more, about 7 N or more, or about 10 N or more. The increase in load or the change in load may be about 50 N or less, about 30 N or less, about 20 N or less, or about 15 N or less. The change in load on the bias member may exponentially increases as a distance of the latch unit form a home position increases. The change in load may be sufficiently large so that the bias member returns the latch unit back to the home position when the latch unit moves from a locked state to an unlocked state, in an unlockable state, a lockable state when the hook latch is not biased, or a combination thereof. The bias member may be a double acting bias member. The bias member may bias towards the home position regardless of whether the bias member is biased in a first direction or a second direction. The bias member may be compressed, expanded, or both when the hook latch is contacted by the bar and the bar moves relative to the hook latch.

The hook latch may function to create the locked state. The hook latch may function to catch the bar and prevent movement of the movable member relative to the ground member. The hook latch may have two sides or more, three sides or more, or four sides or more. The hook latch may have a first side that assists in creating a locked state. The hook latch may have a second side that assist in retaining a bar so that the locked state is maintained. The hook latch may have a third side that assists in creating an unlocked state. The hook latch may be generally triangular in shape or may have a portion that is triangular in shape. The hook latch when contacted may longitudinally move the latch plate. The hook latch when contacted may move in a first direction that expands or contracts the bias member from a home state so that a load is applied to the bias member, energy is stored in the bias member, or both. The hook latch when contacted may move in a second direction that expands or contracts the bias member from a home state so that a load is applied to the bias member, energy is stored in the bias member, or both. Preferably, the hook latch when moved in a first direction will expand the bias member and when moved in a second direction will compress the bias member. The hook latch may include an angled portion, a linear portion, an entry apex, an entry portion, a return portion, an exit apex, pocket, or a combination thereof.

The one or more entry portions may function to assist in creating a locked state when the bar contacts the one or more entry portions. All or a portion of the one or more entry portions may be aligned with the latching pathway when the selection plate is in the lockable state. The one or more entry portions may be mis-aligned with the latching pathway when the selection plate is in the unlockable state. An end of the entry portion (e.g., entry apex) may be located a distance from the bar so that the bar cannot extend to the end of the entry portion as the bar moves along the entry portion. The one or more entry portions may be located a distance away from the bar when the entry portion is in the unlockable state so that the bar cannot contact the entry portion, extend a length of the entry portion, or both. The one or more entry portions may be an angled portion that may be angled so that all or a portion of the one or more angled portion extends across an opening of the latching pathway. The entry portion may extend perpendicular to a longitudinal axis of the handle, the latch plate, or both. Preferably, the entry portion extends at an angle of about 90 degrees or less, about 75 degrees or less, about 60 degrees or less, about 45 degrees or less, or about 30 degrees or more relative to the longitudinal axis of the handle, the latch plate, or both. The one or more entry portions may extend in the path of the prescribed motion of the bar so that the bar contacts the entry portion. The entry portion may be angled so that as the bar extends along the prescribed motion the bar is moved towards the entry apex and ultimately the pocket. The entry portion may have a sufficiently small angle so that as the bar moves along the entry portion the latch plate is moved, compressing or extending the bias member, by a force being exerted upon the entry portion of the hook latch. The latch plate may continue to move as the bar travels along the entry portion until the bar reaches the entry apex. The entry portion may terminate at an entry apex.

The entry apex may function to assist the bar in entering the pocket, leaving the entry portion, or both. The entry apex may be a part of the hook latch. The entry apex may prevent the bar from exiting the pocket from a same direction the bar entered the pocket. The entry apex may be where two walls converge together. The entry apex may be where the entry portion and the curved portion converge. The entry apex may be a point where a bar may be required to be on a first side or a second side of the hook latch. The entry apex may create a lip at the pocket so that the bar cannot be back driven. When the bar passes the entry apex the bias member may release its stored energy so that the bar is moved into the pocket. When the hook latch, the latch plate, or both are in the unlockable state the bar cannot reach the entry apex, the entry apex is moved a distance from the movement unit so that the movement unit is free of contact with the entry apex, or both. For example, when the latch plate is moved to an unlockable state the bar cannot pass an entry apex of the hook latch to create a locked state. When the hook latch, the latch plate, or both are in the lockable state the bar may extend around the entry apex into the pocket. The entry apex and an exit apex may be located on opposing sides of the pocket, the curved wall, or both.

The pocket may function to receive the bar so that a locked state is formed. The pocket functions to restrict movement of the bar. The pocket may be a wall that the bar is biased against so that the bar is restricted from being moved back into the latching pathway. The pocket may be a curved portion of the hook latch. The pocket may be located proximate to the wall guide. The pocket may be a recess that the bar resides within so that the locked state is formed and the bar is not inadvertently moved out of the pocket. The pocket may resist a biasing force of the movable member away from the ground member. For example, the movable member may be biased away from the ground member and the pocket may resist the bar from exiting the pocket. In another example, the trigger may be biased apart from the hand piece by a bias device and the bias device may assist in moving the bar into the pocket. The pocket may resist a bias force in a lateral direction, a longitudinal direction, or both. The pocket may resist the biasing member from moving to the home position. The pocket may prevent longitudinal movement, lateral movement, or both of the bar. The exit apex, the entry apex, or both may extend beyond the pocket so that the bar remains within the pocket until a bias force of the movable member is resisted, a user regrips the movable member and the ground member together, or both. Upon regripping, resisting a bias force, or both the bar may exit the pocket by extending around the exit apex.

The exit apex may function to prevent a bar from inadvertently exiting the pocket, the curved portion, or both. The exit apex may extend beyond the pocket. The exit apex may be where the return portion and the curved portion converge. The exit apex may be a point that once the bar extends beyond the bar cannot reenter the pocket. The bar may contact the exit apex while exiting so that the latch plate is biased, and upon the bar stopping contact with the exit apex, the latch plate may bias away from the bar, to the home position, or both so that the prescribed motion of the bar is above the pocket and the bar cannot reenter the pocket. The exit apex may be formed between the pocket and the return portion.

The return portion may function to guide the bar from the locked state to an unlocked state. The return portion may function to guide the bar to the latching pathway. The return portion may be located below the prescribed path when the latch plate is in the home position. Preferably, the return portion is located below an upper portion of the pathway when the hook latch is in the home position. The return portion may be a linear portion. The return portion may be located above the latch plate when the latch plate is in the home position. For example, the hook latch may block the latching pathway when the latch plate is in the home position, and as the bar moves along a prescribed path the bar may contact the return portion of the hook latch and move the hook latch to open the latching pathway. For example, the bar may push the hook latch down by contacting the return portion so that the release apex is located below the latching pathway and the bar can exit the handle, the hand piece, the latch unit, housing, or a combination thereof. As the latching pathway is being opened the bias device may be compresses an energy stored within the bias device. Once the bar stops contacting the return portion (e.g., leaves the pathway) and reenters the latching pathway the bias device may bias the latch plate back to a home position. The return portion may be moved into alignment with the latching pathway when the bar moves along the pathway towards the latching pathway.

The pathway may function to guide the bar from a home position to a locked position, from a locked position to an unlocked position, from an unlocked position to a home position, or a combination thereof. The pathway may align with the latching pathway, the bar pathway, the bar arm pathway, or a combination thereof. The pathway may be out of alignment with the latching pathway. The pathway may assist a bar in circumnavigating a hook latch, the pathway may extend around the hook latch, or both. The pathway may be tortuous. The pathway may be a labyrinth. The pathway may be an open area in the movement unit that the bar is guided through. The pathway may be an area between two or more walls that a bar moves through, a bar moves along, or both. The pathway may be linear or have linear portions. The pathway may have curved portions, arcuate portions, straight portions, extend 360 degrees, have serpentine portions, or a combination thereof. The pathway may begin and end at a latching pathway. The pathway may extend along an entry portion, along a return portion, around an entry apex, into a pocket, around an exit apex, into a wall guide, around a guide apex, around a release apex, along a rear wall, or a combination thereof. The pathway may assist the bar in moving along one or more walls of the hook latch. The pathway may assist the bar in moving the latch plate as the bar and the hook latch contact each other. The pathway may be out of alignment with the hook latch, the wall guide, or both when the latch unit is in the unlocked position, the unlocked state, the unlockable state, or a combination thereof. The pathway may extend between the hook latch and the wall guide. The pathway may permit the bar to move around the release apex of the hook latch, move into contact with the wall guide, or both.

The release apex may function to guide the bar into the pathway and out of the pathway. The release apex may align an entry end of the pathway with the latching pathway when the latch unit is in the lockable state, unlocked state, or both. The release apex may align an exit end of the pathway with the latching pathway when the latch unit is in the lockable state, unlocked state, or both. The release apex may move from a first side of a latching pathway to a second side of a latching pathway. The release apex may be located in an upper half of the latching pathway when the hook latch is in the home state. The release apex may connect the pathway to the latching pathway. The release apex may form a point of the hook latch. The release apex may be a beginning and end of the hook latch. The release apex may be located opposite the pocket. The release apex may be located opposite the wall guide.

The one or more wall guides may function to assist the bar in moving from a locked position to an unlocked position, an unlocked position to a locked position, or both. The one or more wall guides may restrict movement in a first direction (e.g., vertically, towards a forward post), in a vertical direction, or both when the bar is moving from an unlocked position to a locked position. The one or more wall guides may assist a bar in extending around an entry apex, an exit apex, or both. The one or more wall guides may extend into the pathway to restrict movement of the bar. The one or more wall guides may include a guide apex and a rear wall. The one or more wall guides may include a guide wall and a guide apex that extends into the pocket, towards the hook latch, or both. The guide wall and the guide apex may direct the bar into the pocket when the bar extends around the entry apex.

The one or more guide walls may function to direct the bar towards or into the pocket. The one or more guide walls may prevent the bar from extending around the entry apex and the exit apex. The one or more guide walls may extend parallel to the entry portion. The one or more guide walls may extend from outside of the pocket to a location proximate to the pocket. The guide wall may be linear. The guide wall may interrupt the pathway. The one or more guide walls may be located below the guide apex. The one or more guide walls may connection to the rear wall forming a guide apex.

The one or more guide apexes may function to prevent the bar from moving through the pocket without a locked state being formed, without the bar being in the locked position, or both. The one or more guide apexes may divide a pocket in half. The guide apex may be located between the entry apex and the exit apex. The guide apex may be substantially linear, angled downward, angled toward the entry apex, or both. The guide apex may overlap the exit apex. For example, a mid-point extending between the hook latch and the wall guide may be crossed by both the hook latch and the wall guide. The guide apex may interfere in the pathway so that as the bar moves around the entry apex the bar may contact the guide apex so that when a trigger, a movable member, or both are released the bar moves the pocket. The guide apex may not contact the bar but may guide the bar into contact with the exit apex so that the bar is retained within the pocket and a locked state is created. The guide apex may be located under a rear wall. The guide apex may connect to the wall and the rear wall may connect the guide apex to the wall.

The rear wall may function to guide the bar around the exit apex. The rear wall may extend at an angle relative to the guide apex. The rear wall may angle away from the exit apex towards a wall. The rear wall may extend away from the exit apex. The rear wall may extend from a location below the exit apex to a location above the exit apex. The rear wall may guide the bar around the exit apex as a user applies a force to the trigger, the movable member, or both so that the bar moves away from the pocket towards the rear wall. The rear wall may include one or more curves. The rear wall may include a concave region, a convex region, or both. The rear wall may guide the bar as the bar moves along a prescribed motion, an arcuate movement, or both.

The arcuate movement may function to move the bar from a home position, to a locked position, to an unlocked position, or a combination thereof. The arcuate movement may be an arcuate locking path, an arcuate release path, an arcuate trigger path, or a combination thereof. The arcuate movement may travel a same path in a forward direction as a backward direction. The arcuate movement may be a movement of the bar, the trigger, a movable member, or a combination thereof as the bar, the trigger, a movable member, or a combination thereof rotate about a pivot. The arcuate movement may be a prescribed movement of the bar, the trigger, the movable member, or a combination thereof. The arcuate movement may be the only movement the trigger, the bar, the movable member, or a combination thereof makes. The arcuate movement may move the bar from a home position to a locked position, a locked position to an unlocked position, and an unlocked position back to a home position.

The home position may be a position where the latch plate is at steady state, the bar is not within the latch unit, or both. The home position may be a position where the bias member is free of compression. The latch plate in the home position may be at a zero load, zero force, or both. The latch plate may move from a locked position to a home position or vice versa, an unlocked position to a home position or vice versa, or both. The home position may be where the hook latch crosses the latching pathway. The home position may be where the bias member returns the latch plate upon an engagement force or a disengagement force being removed. The home position may be where the movement unit and the latch unit are disconnected, can move relative to each other, or both. The bar may move from an unlocked position to a home position and be free of a home position. The bar may move from a locked position to an unlocked position and then to a home position.

The locked position may be where the bar is located within the pocket and the bar is prevented from moving by the hook latch. The locked position may be where the bar is located between the entry apex and the exit apex. The locked position may be where the movable member moves the bar back towards the hook latch so that the bar is retained in the pocket and the movable member is prevented from moving. The locked position may be the position where the bar prevents the movable member, a trigger, or both from moving. The locked position may be where the hook latch is aligned with the latching pathway. In the bar moving to the locked position (e.g., a forward stroke), the bar may bias the hook latch up or in a first direction (i.e., towards a forward post) as the bar enters the pathway. In the bar moving from the locked position (e.g., a return stroke), the bar may bias the hook latch down or in a second direction, which is opposite the first direction as the bar exits the pathway. In the locked position, the hook latch may be moved by the bar as the bar moved along the arcuate movement, the pathway, or both. In the locked position, the bar may remain static and be prevented from moving. The latch plate may be locked by the locked state detent when the latch unit is in the locked position. The locked position may be located between two unlocked positions.

The unlocked position may function to allow the bar to move within the pathway. The unlocked position may be any position where the bar is within the pathway but not located within the pocket. The unlocked position may be a bar in the pathway moving along the entry portion, the return portion, or both. The unlocked position may be where the bar is not located between the entry apex and the exit apex. The bar may make a locking movement so that the bar changes from an unlocked position to a locked position.

The locking movement may be where the bar extends from an unlocked position to a locked position. The locking movement may be where the bar extends around an entry apex. The locking movement may be where the bar moves into contact with the guide apex and then upon release of the trigger, the movable member, or both the bar is moved into the pocket, from the guide apex into the pocket, into contact with the exit apex but retained in the pocket, or a combination thereof. The locking movement may be where the bar enters the pocket. As the bar makes a locking movement the bar may bias the bias member so that the bias member has a load. Once the bar completes the locking movement and moves into the pocket the bias member may retain some load The locking movement may be followed by an unlocking movement where the bar is released from the pocket.

The unlocking movement may function to release the bar from the pocket. The unlocking movement may be a movement around the exit apex. The unlocking movement may be a movement from the pocket to the wall guide where the wall guide assists in moving the bar around the exit apex, to a location above the exit apex, or both. The unlocking movement may extend away from the hook latch and then back towards the hook latch once the bar is above the exit apex. Once the bar extends around the exit apex the hook latch may move back to a home position where the hook latch, bias device, or both have a zero load. The unlocking movement may result in the bar being in an unlocked state. An unlocking movement may move the selection plate between a lockable state and an unlockable state. The unlocking movement may be followed by a resetting movement where the bar is moved back to a starting position, the bar moves out of the latch unit, the trigger and handle move back to a home position, or a combination thereof. The resetting movement may function to reset the bar. The resetting movement may be a movement around the release apex, through the latching pathway, or both. The resetting movement may result in the bar being in an unlocked state. The resetting movement may be a movement along the return portion of the hook latch, through the latching pathway, or both. The resetting movement may be the bar moving along a portion of an arcuate release path. A resetting movement may move the selection plate between a lockable state and an unlockable state. The resetting movement may bias the latch plate in a second direction so that the bar aligns with the latching pathway, can extend around the release apex, or both. The unlocking movement may be followed by a resetting movement where the bar is moved towards the release apex, around the release apex, or both. The resetting movement may be a movement of the bar towards the latching pathway regardless of if the latch unit is in the lockable state, the unlockable state, or both.

The unlockable state may be a state where the detent pin is located within the unlockable state detent. The unlockable state may function to prevent the closure assembly to be locked. The unlockable state may be a state where the latch unit is configured to be out of a movement path of the movement unit so that a locked state cannot be formed. The unlockable state may be where the latch state is moved to a second position where the latch unit and the movement unit are not aligned, a distance is too great for the bar to travel to the pocket, or both. Preferably, the hook latch in the unlockable state maintains alignment along the prescribed path but the hook latch is moved a greater distance from the bar so that the bar cannot lock with the hook latch. The unlockable state may be where the hook latch is mis-aligned with the latching pathway so that as a bar extends into the latching pathway the bar and hook latch do not contact each other. In the unlockable state the hook latch may be located entirely above or below the latching pathway. The unlockable state may be a state where the detent pin is located within the unlockable state detent. When the latch plate is moved from the unlockable state detent to the lockable state detent the closure assembly may change from the unlockable state to the lockable state.

The lockable state may function to allow the closure assembly to be latched. The lockable state may be a state where the movement unit and the latch unit are aligned and may connect together, may lock a movable member to a ground member, or both. The lockable state may be where a portion of the hook latch is aligned with the latching pathway so that as a bar extends through the latching pathway the bar can contact the hook latch to create a locked state. When the latch unit is in the lockable state the bar may extend around an entry apex into a pocket to create a locked state. In the lockable state, the bar may contact the hook latch and move the movement unit. The closure assembly, in the lockable state may have an unlocked state or a locked state. The unlocked state may be where the movable member and the ground member are movable relative to each other. The unlocked state may be where the bar is not constrained by the latch unit. The unlocked state may be where the latch unit is not locked relative to the movement unit and the latch unit and the movement unit may move relative to each other. The unlocked state may be where the latch plate is locked so that the bar extends into the pathway and is not constrained any members of the latch plate, the hook latch, or both. The unlocked state may allow a user to freely open and close the jaws without the jaws being locked in place. The latch plate, in the unlocked state, may be locked in a position so that the movable member and the ground member are unlocked. The unlocked state may be where the latch unit is in a lockable state but the bar is not located within the pocket so that the bar is movable relative to the hook latch. The bar in the unlocked state may be in contact with any part of the hook latch except for the pocket. The latch unit may in a lockable state and changed between a locked state and an unlocked state, the bar may be movable between a locked state and an unlocked state, or both.

The locked state may function to lock the movable member and the ground member together. The locked state may be where the closure assembly is locked. The locked state may be where the movement unit and the latch unit are connected together. The locked state may be where the latch unit is moved along the sliding axis and restrained by the bar. The locked state may be where the latch unit, the hook latch, or both are movable by the movement unit to lock the movable member and the ground member together. The locked state may be where the bar is located within a pocket. The locked state may be where the latch plate is restricted from moving about a sliding axis by the bar.

The sliding axis may function to move the latch plate from a first position to a second position, along the track, up and down, parallel to a length of the handle, or a combination thereof. As the latch plate moves along the sliding axis compression of the bias member may be increased, decreased, or a combination of both. The as the bar moves along the hook latch, an engaging force may be applied to the hook latch that moves the latch plate along the sliding axis.

The engaging force may function to move the latch plate along the sliding axis, to compress the bias member, to lock the closure assembly, to lock the movement unit to the latch unit, or a combination thereof. The engaging force may be sufficiently large to move the latch plate as the bias member compresses or stretches. The engaging force may increase as the bar moves along the hook latch. The engaging force may increase as the bar moves from the release apex towards the entry apex. The engaging force may increase as the bar moves along the return portion. The engaging force may increase as the bar moves from the exit apex to the release apex. Preferably, the engaging force is along a first side of the hook latch, along the entry portion, or both as the bar extends from the latching pathway and the pathway and into the pocket. The engaging force may be a single force that is generated by a user as the bar moves along a prescribed movement an arcuate movement, or both. The user may generate the engaging force by moving the movable member and the ground member towards each other. The engaging force may be substantially similar to an amount of force required for a disengaging force.

The disengaging force may function to move the bar out of the pocket, around the exit apex, or both. The disengaging force may extend parallel to the engaging force. The disengaging force may have one or more forces along one or more different directions, vectors, or both. The disengaging force may remove a bar from the pocket and then remove the bar from the latch unit, the housing, the handle, the hand piece, or a combination thereof. The disengaging force may have a portion that is along the exit apex, along the wall guide, along the return portion, or a combination thereof. The disengaging force may be created by a regripping and movement of the movable member relative to the ground member. The disengaging force may first extend away from the hook latch, then up the rear wall, around the exit apex, and then along the return portion where the latch plate is moved along the sliding axis. The disengaging force may have a first disengaging force where the bar is moved out of the pocket and a second disengaging force where the bar is aligned with the latching pathway. The first disengaging force may move the bar away from the pocket (i.e., a regrip of the movable member or the trigger), up over the exit apex, or both. The first disengaging force may guide the bar along a rear wall of the wall guide. The first disengaging force may release the closure assembly, move the closure assembly from a locked state to an unlocked state, or both. Once the bar, movement unit, or both are released the bar, movement unit, or both may change from a first disengagement force to a second disengagement force. The second disengagement force may move the latch plate along the sliding axis so that the bar is aligned with the latching pathway. The second disengagement force may be sufficiently large to compress the bias member. The second disengagement force may increase as the bar moves along the prescribed motion, the arcuate movement or both. The second disengagement force may move the latch plate from a home position to an unlocked position where the bar may separate from the latch unit.

FIG. 1 illustrates a top perspective view of an electrosurgical device 2 that is configured as forceps 10. The electrosurgical device 2 includes a handpiece 4 that is attached to a movable member 12 and a ground member 14. The movable member 12 is a first working arm 20 including a first jaw 16 and the ground member 14 is a second working arm 22 including a second jaw 18. A closure assembly 40 assists in maintaining the first working arm 20 and the second working arm 22 in a closed state when the closure assembly 40 is activated.

Figure 2:
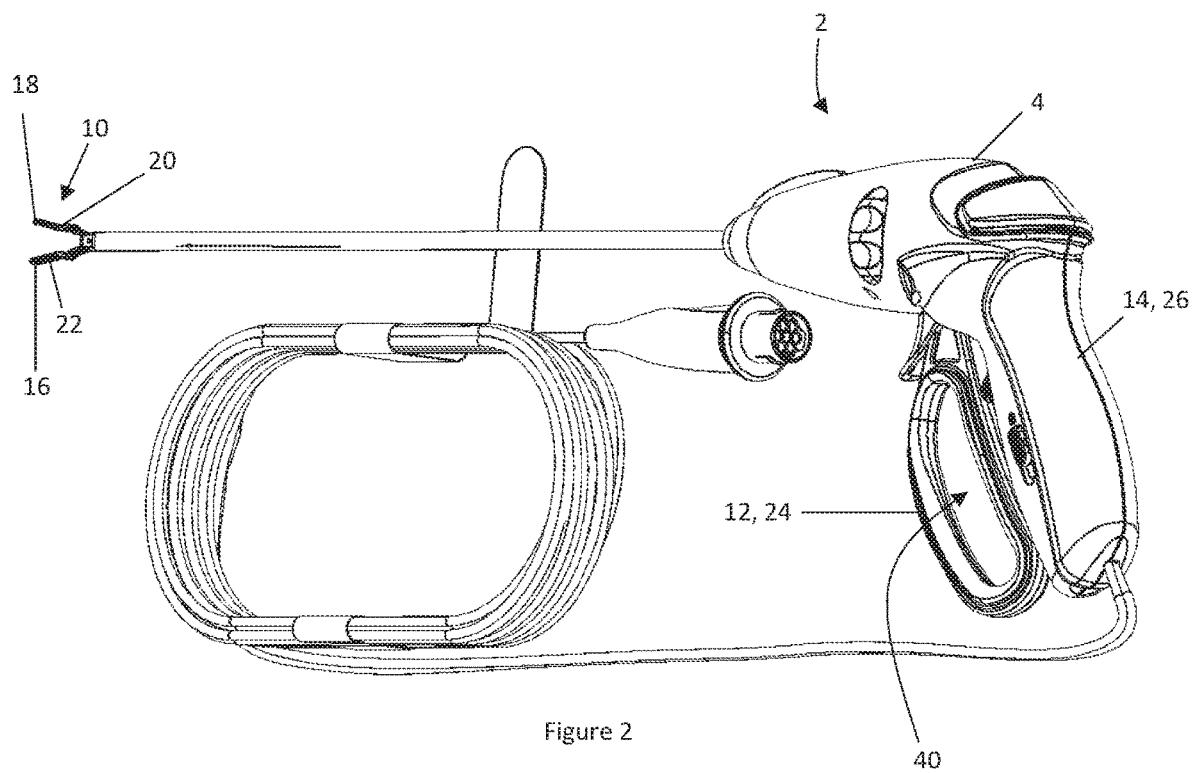
FIG. 2 is a perspective view of an electrosurgical device having a latching assembly.

FIG. 2 is a rear perspective view of an electrosurgical device 2 including a handpiece 4 and forceps 10. The forceps 10 include a first working arm 20 with a first jaw 16 and a second working arm 22 with a second jaw 18. The handpiece 4 includes a closure assembly 40 that prevents movement of the first working arm 20 and the second working arm 22 by locking the movable member 12 and the ground member 14 in a position. The movable member 12 is a trigger 24 and the ground member 14 is a handle 26.

Figure 3A:
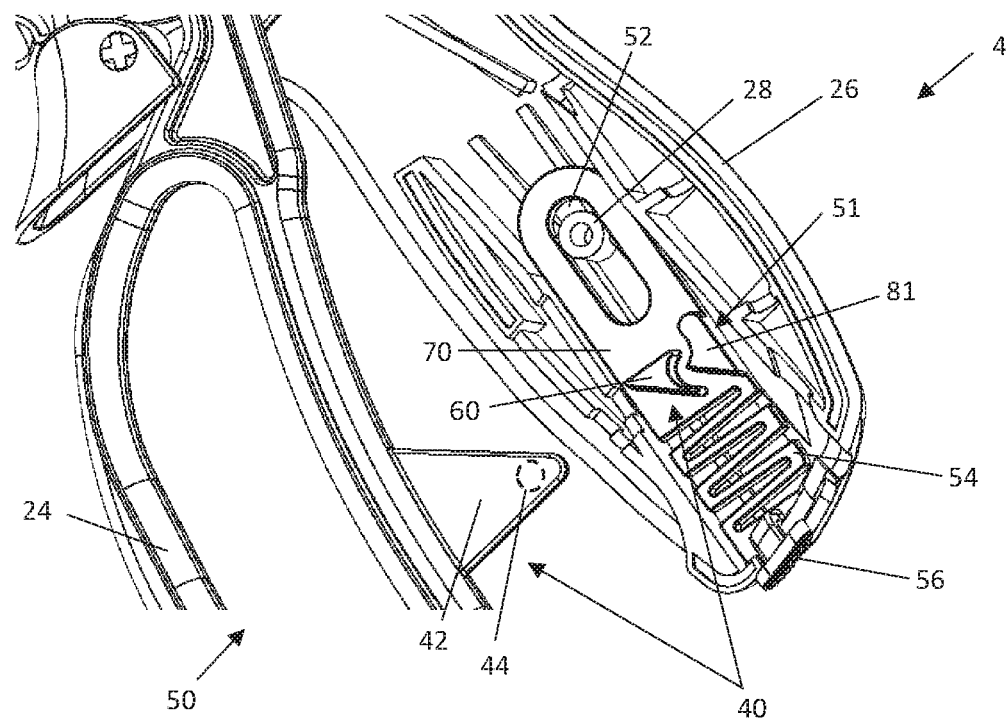
FIG. 3A is a close-up cross-sectional view of a movement unit and a latch unit in a lockable state.

FIG. 3A illustrates a laterally bisected perspective view of a handpiece. A closure assembly 40 includes the latch unit 51 and a movement unit 50. The movement unit 50 includes a trigger 24, a bar arm 42, and a bar 44. The bar 44 is fixed to the bar arm 42, which is fixed to the trigger 24. The latch unit 51 includes a bias member 54, an adjustment switch 56, a latch plate 70, a hook latch 60, and a wall guide 81. The latch plate 70 includes a guide aperture 52, which is configured to accept a connection pin 28 fixed to the handle 26. Further, the hook latch 60 and a wall guide 81 are fixed to the latch plate 70.

Figure 3B:
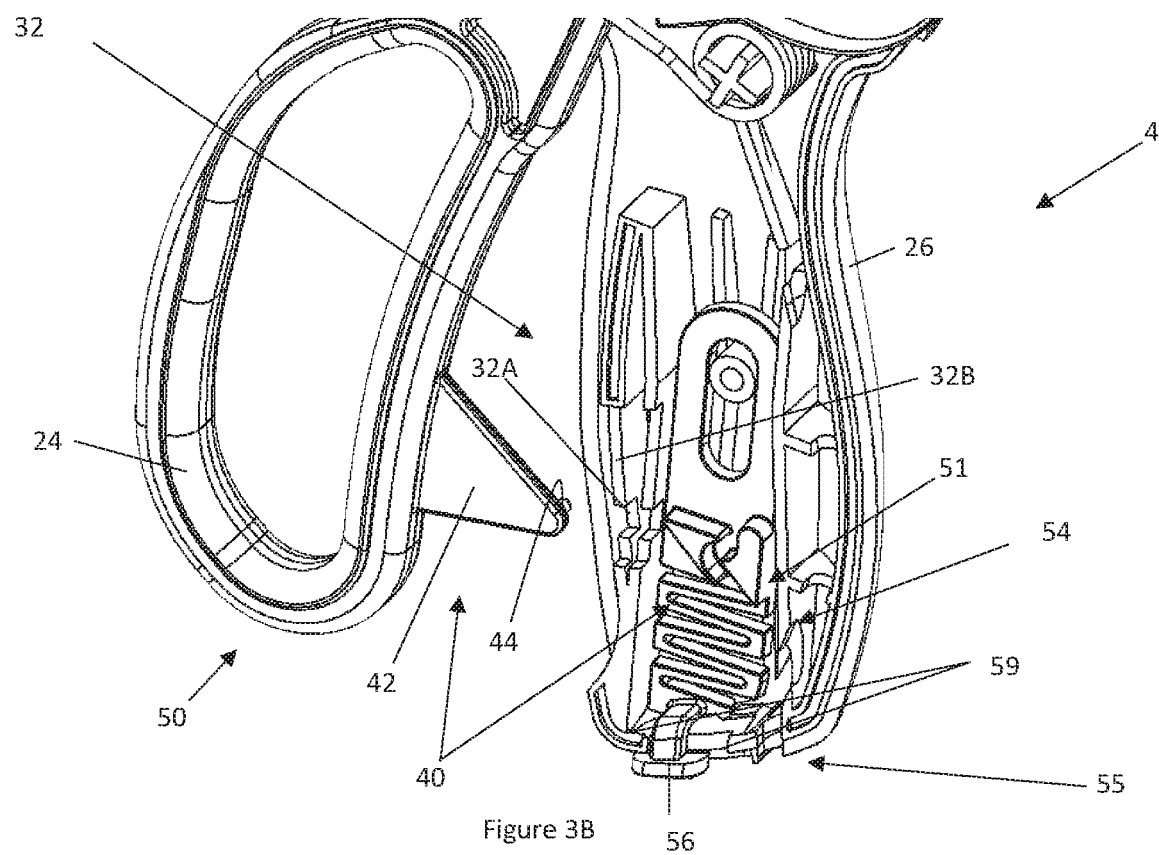
FIG. 3B is a close-up cross-sectional view of a movement unit and a latch unit in a lockable state.

FIG. 3B illustrates a laterally bisected perspective view of the handle 4 including a closure assembly 40 having a latch unit 51 and a movement unit 50. The movement unit 50 includes a trigger 24 with a bar arm 42 and a bar 44 extending form the bar arm 42 with the bar 44 being aligned with a latching pathway 32 of the latch unit 51 that is formed in the handle 26. The latching pathway 32 includes a bar pathway 32A that allows the bar to extend into the latch unit 51 and a bar arm pathway 32B that is shallower than the bar pathway 32A and permits the bar arm 42 to extend into the latch unit 51. The latch unit 51 includes a selection plate 55 with an adjustment switch 56 that extends out of the handle through a compression stop 59 that restricts movement of the bias member 54.

Figure 4:
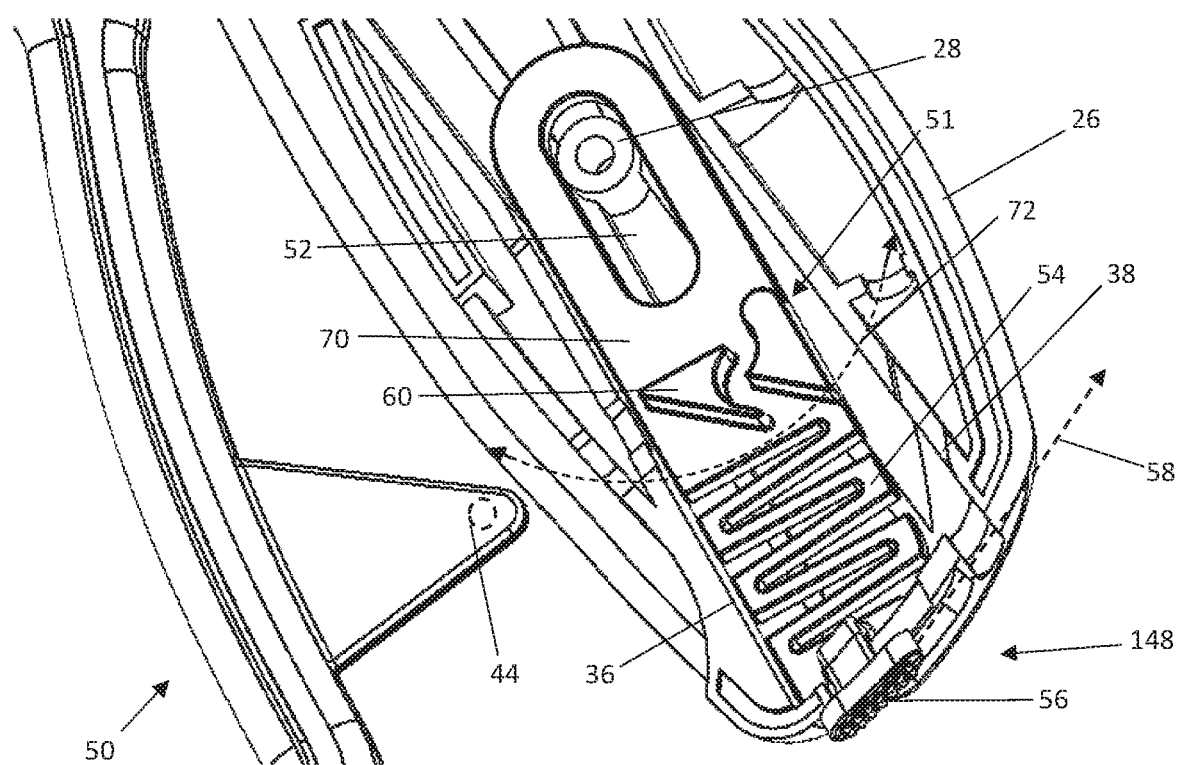
FIG. 4 is a close-up view of a movement unit and a latch unit and the prescribed motion of the movement unit.

FIG. 4 illustrates a close-up, laterally bisected perspective view of the latch unit 51 in a lockable state 148 so that the movement unit 50 is aligned with the latch unit 51. The adjustment switch 56 is movable along a switch path 58 selectively between the lockable state 148 to an unlockable state (not shown). The handle 26 includes a forward stop 36 and a backward stop 38, which define the boundaries of the latch unit's 51 movement along the switch path 58. The adjustment switch 56 is connected to the bias member 54 and latch plate 70 so that the latch plate 70 is movable along a latch plate path 72 by the guide aperture 52 sliding along the connection pin 28.

Figure 5A:
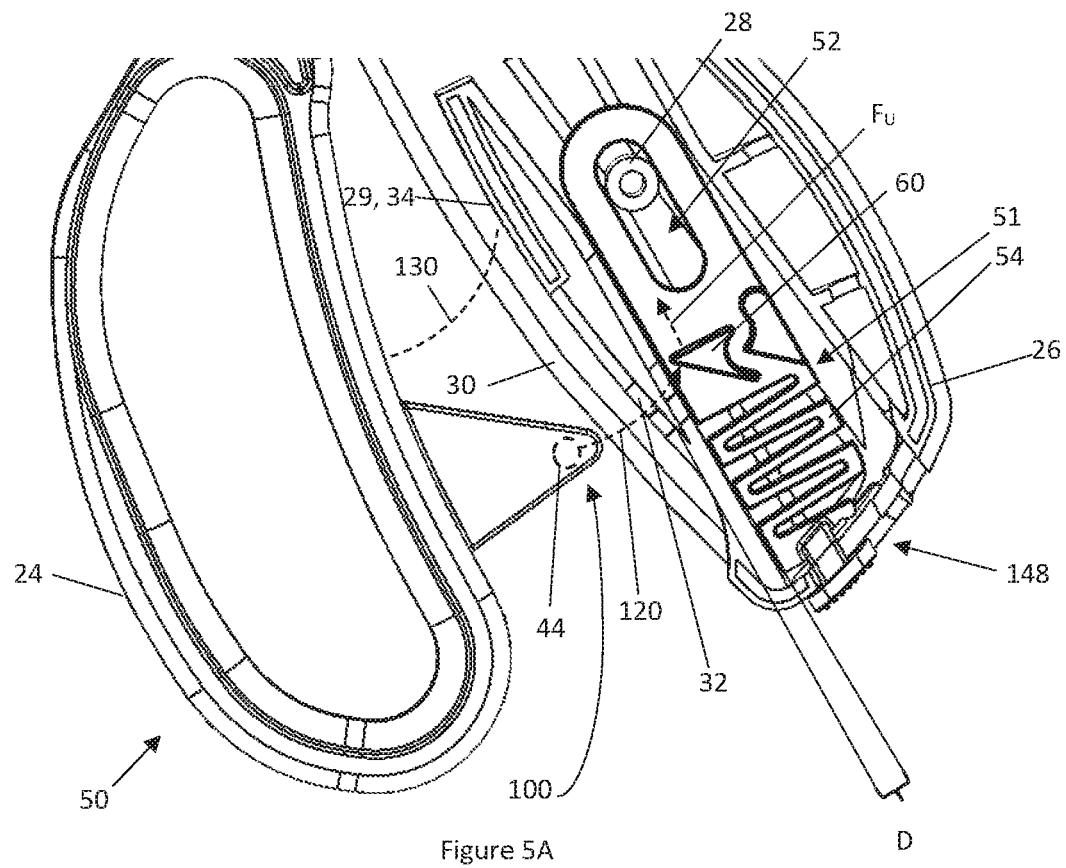
FIG. 5A is a close-up view of a movement unit and a latch unit in a lockable state.

FIG. 5A illustrates a laterally bisected, perspective view of the latch unit 51 in the lockable state 148 where the latch unit 51 is located a distance (D) from the latching pathway 32. An aperture 30 is formed in the handle 26 and is configured to accept the bar 44 of the trigger 24. When pressure is applied to the trigger 24 of the movement unit 50, the trigger 24 moves along an arcuate trigger path 130 into the aperture 30 and reaches a terminus as the trigger 24 contacts the sidewall 34, which as shown acts as a trigger stop 29. The bar 44 moves along an arcuate locking path 120 from a home position 100, through the latching pathway 32, and contacts the hook latch 60, imparting an engaging force FU on the hook latch 60. The engaging force FU results in movement of the hook latch 60 and latch plate 70 along a connection pin 28 that extends into the guide aperture 52. As the bias member 54 moves from the engaging force FU being applied to the hook latch 60 energy is stored in the bias member 54.

Figure 5B:
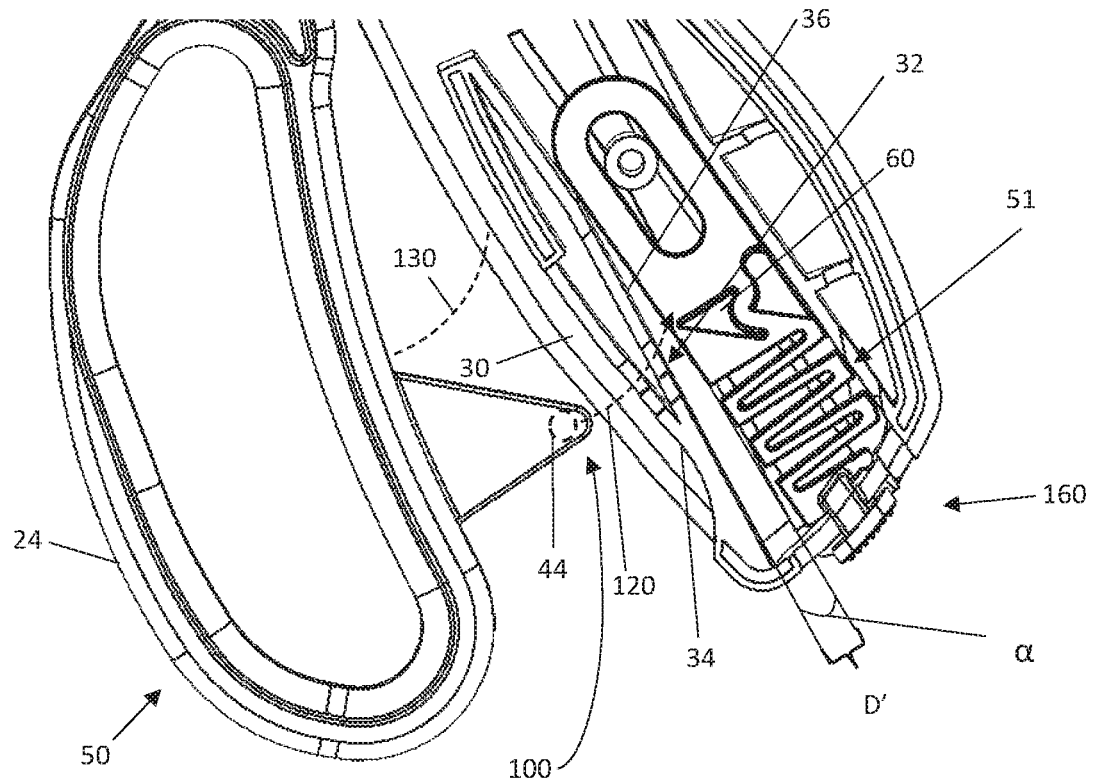
FIG. 5B is a close-up view of a movement unit and a latch unit in an unlockable state with a portion the selection plate removed from the latch unit.

FIG. 5B illustrates a laterally bisected perspective view of the latch unit 51 in an unlockable state 160. In the unlockable state 160, the latch plate 70 and hook latch 60 are located a distance (D') away from the latching pathway 32 and the bar 44 so that when pressure is applied to the movement unit 50, the trigger 24 moves along the arcuate trigger path 130 into the aperture 30 and the bar 44 is either stopped before reaching the hook latch 60 as the trigger 24 contacts the sidewall 34 or the bar 44 moves along the arcuate locking path 120 and passes by the hook latch 60 without contacting the hook latch 60 so that the trigger 24 freely moves between a home position 100 and a closed position that is not locked. An angle (a) is located between the latch plate 70 and the forward stop 36.

Figure 6A:
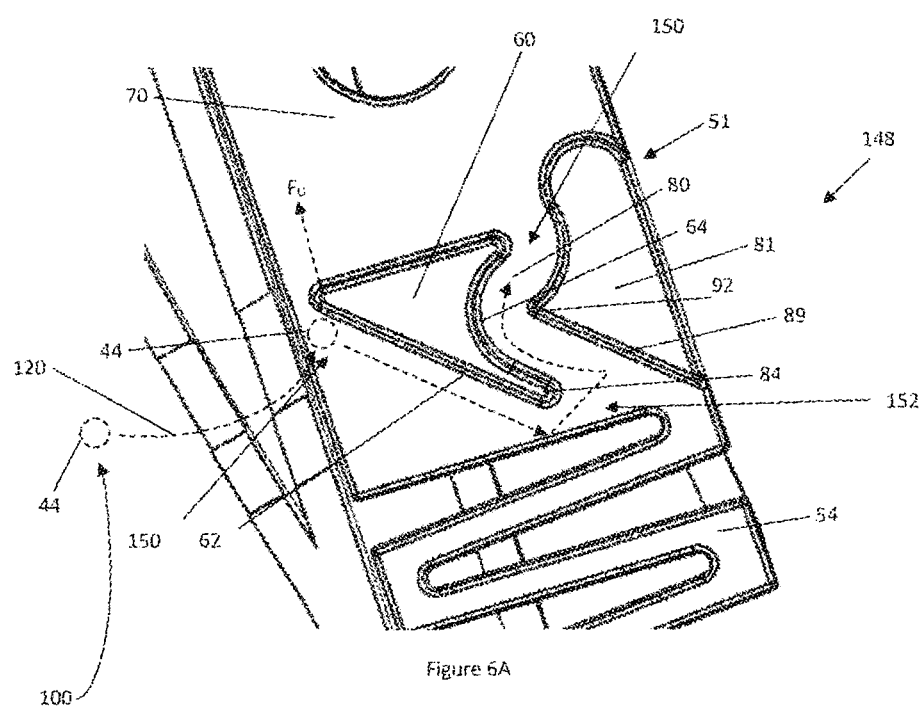
FIG. 6A is a close-up view of the latch plate showing a pathway as a bar moves from an unlocked state to a locked state.

FIG. 6A illustrates a close-up view of the latch unit 51 and latch plate 70 in the lockable state 148. When pressure is applied to the trigger (not shown) the bar 44 moves from the home position 100, along the arcuate locking path 120, and contacts an entry portion 62 of the latch plate 60 thereby applying the engaging force FU to the hook latch 60. The engaging force FU causes the bias member 54 to lengthen and increase in potential energy stored within the bias member 54. As the bar 44 travels along the path 122, the hook latch 60 continues to move in the direction of the engaging force FU and the potential energy of the bias member 54 increases until the bar 44 passes an entry apex 84 from an unlocked state 152 to a locked state 150. Once past the entry apex 84, the bar 44 moves along a path 124 and contacts a guide wall 89 and guide apex 92 of the wall guide 81 until the bar 44 settles into a pocket, creating a locked state 150, that is formed by a curved portion of the hook latch 60. Once the bar 44 is past the entry apex 84 and pressure is released from the trigger (not shown), the bias member 54 moves the hook latch 60 in a direction opposite the direction of the engaging force FU so that the bar 44 moves along path 124 into the curved portion 64, which prevents the bar 44 and trigger (not shown) from being moved.

Figure 6B:
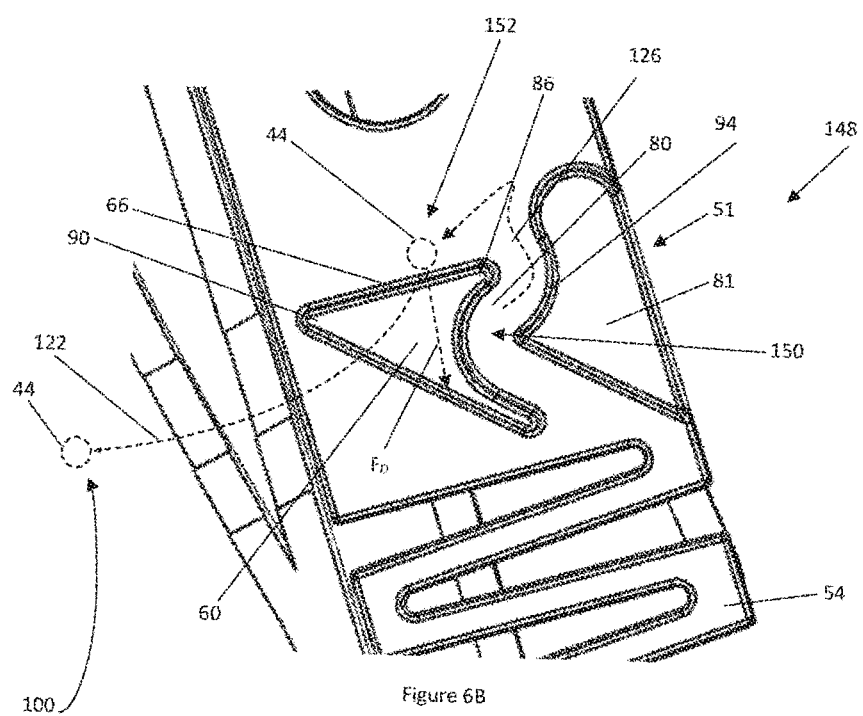
FIG. 6B is a close-up view of the latch plate showing a pathway as the bar moves from a locked state to an unlocked state.

FIG. 6B illustrates a close-up view of the latch unit 51 in the lockable state 148. When pressure is applied to the trigger (not shown), the bar 44 travels along the rear wall 94 and the path 126 where the bar 44 moves from a locked state 150 the pocket 80 along a rear wall 81 and past an exit apex 86 to an unlocked state 152. When pressure is released from the trigger (not shown), the bar 44 applies a disengaging force FD against a return portion 66 of the hook latch 60, causing the potential energy of the bias member 54 to increase by shortening the bias member 54. The disengaging force FD persists as the bar 44 moves along an arcuate release path 128 until the bar 44 passes a release apex 90 and moves to the home position 100.

Figure 7A:
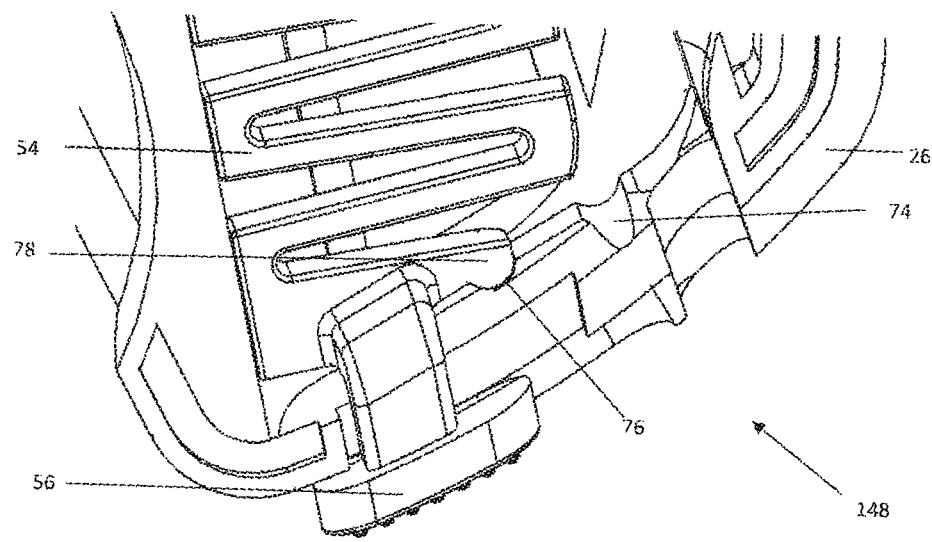
FIG. 7A is a close-up view of the adjustment switch in the lockable state.

FIG. 7A illustrates a close-up view of the adjustment switch 56 in the lockable state 148. The bias member 54 includes a detent pin 78 that is located within a lockable state detent 76 so that the adjustment switch 56 is locked in place relative to the handle 26. The handle 26 also includes an unlockable state detent 74.

Figure 7B:
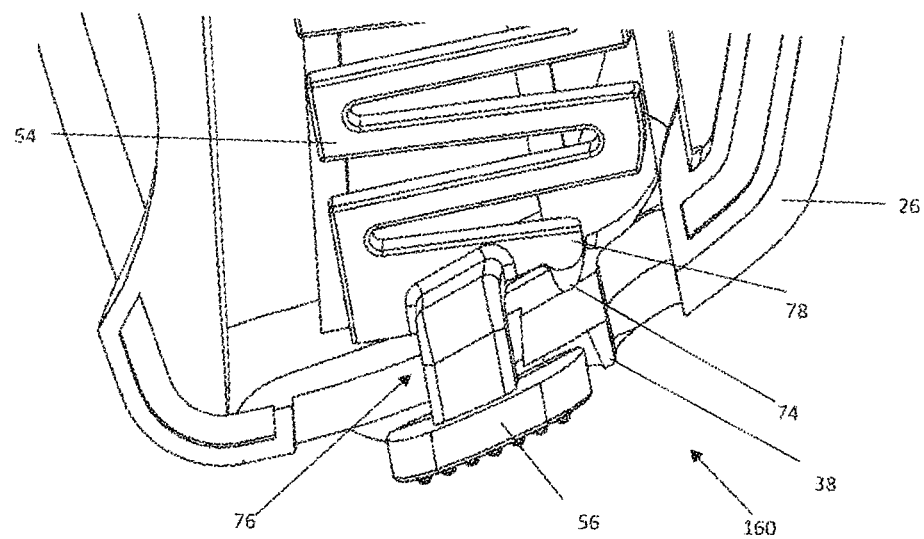
FIG. 7B is a close-up view of the adjustment switch in the unlockable state.

FIG. 7B illustrates a close-up view of the adjustment switch 56 moved from the lockable state detent 76 to the unlockable state detent 74 so that an unlockable state 160 is formed. The bias member 54 includes a detent pin 78 that is located within the unlockable state detent 74 to retain the adjustment switch 56 relative to the handle 26. The adjustment switch 56 is located proximate to the backward stop 38, which prevents the detent pin 78 from overrunning the unlockable state detent 74

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A closure assembly for a surgical device comprising:
a movement unit including a bar that moves in a direction of a prescribed motion; and
a latch unit including a latch plate including a hook latch that selectively receives the bar, the latch plate being movable in the direction of the prescribed motion between a first state and a second state.

2. The closure assembly of claim 1, wherein the latch plate includes a guide aperture and the latch plate is pivotable about the guide aperture.

3. The closure assembly of claim 2, wherein the latch plate is movable longitudinally along the guide aperture.

4. The closure assembly of claim 3, wherein the first state is a lockable state where the hook latch is engageable by the bar of the movement unit.

5. The closure assembly of claim 4, wherein the second state is an unlockable state where the bar does not reach the hook latch or the hook latch is moved out of alignment with the prescribed motion so that the hook latch is not engaged by the bar.

6. The closure assembly of claim 1, wherein the latch plate includes a guide aperture that receives a connection pin of the surgical device.

7. The closure assembly of claim 6, wherein the guide aperture is elongated and has a longitudinal dimension that is greater than a lateral dimension.

8. The closure assembly of claim 1, further comprising an adjustment switch that is operable to move the latch plate between the first state and the second state.

9. The closure assembly of claim 8, further comprising a biasing member positioned between the latch plate and the adjustment switch.

10. The closure assembly of claim 8, wherein the latch plate is movable between a forward stop when the latch plate is in the first state and a rearward stop when the latch plate is in the second state.

11. The closure assembly of claim 10, wherein the forward stop and the rearward stop define boundaries of a switch path upon which the adjustment switch can travel.

12. A closure assembly for a surgical device comprising:
a movement unit including a bar that moves in a direction of a prescribed motion; and a latch unit including a latch plate including a hook latch that selectively receives the bar, the latch plate being movable in the direction of the prescribed motion between a first state and a second state;

wherein the latch plate includes a guide aperture that receives a connection pin of the surgical device; and wherein the latch plate is pivotable about the guide aperture and movable longitudinally along the guide aperture.

13. The closure assembly of claim 12, wherein the latch plate includes a bias member comprising a deformable body.

14. The closure assembly of claim 13, further comprising an adjustment switch that moves the latch plate between the first state and the second state.

15. The closure assembly of claim 14, wherein the adjustment switch includes a detent pin structured to engage a first detent when the latch plate is in the first state and a second detent when the latch plate is in the second state.

16. A closure assembly for a surgical device comprising:
a movement unit including a bar that moves in a direction of a prescribed motion; and
a latch unit including a latch plate including a hook latch that selectively receives the bar, the latch plate being movable in the direction of the prescribed motion between a lockable state and an unlockable state;

wherein the latch plate includes an adjustment switch that moves the latch plate between the first state and the second state.

17. The closure assembly of claim 16, wherein the latch plate includes a guide aperture and the latch plate is pivotable about the guide aperture.

18. The closure assembly of claim 17, wherein the latch plate is translatable along the guide aperture.

19. The closure assembly of claim 16, wherein the latch plate includes one or more bias members.

20. The closure assembly of claim 19, wherein the one or more bias members comprise a deformable body including a plurality of elastically deformable connections that are movable relative to each other to receive energy and release energy.

* * * * *